US012629375B2

(12) United States Patent

Robichaux et al.

(10) Patent No.: US 12,629,375 B2

(45) Date of Patent: *May 19, 2026

(54) COMPOUNDS WITH ANTI-TUMOR ACTIVITY AGAINST CANCER CELLS BEARING HER2 EXON 21 INSERTIONS

(71) Applicant: Board of Regents, The University of Texas System, Austin, TX (US)

(72) Inventors: Jacqulyne Robichaux, Houston, TX (US); John V. Heymach, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1019 days.

This patent is subject to a terminal disclaimer.

(21) Appl. No.: 17/600,017

(22) PCT Filed: Mar. 27, 2020

(86) PCT No.: PCT/US2020/025478

§ 371 (c)(1),
(2) Date: Sep. 29, 2021

(87) PCT Pub. No.: WO2020/205632

PCT Pub. Date: Oct. 8, 2020

(65) Prior Publication Data

US 2022/0175778 A1     Jun. 9, 2022

Related U.S. Application Data

(60) Provisional application No. 62/826,758, filed on Mar. 29, 2019.

(51) Int. Cl.

| | |
|---|---|
| *A61K 31/517* | (2006.01) |
| *A61P 35/00* | (2006.01) |
| *C07K 14/705* | (2006.01) |
| *C07K 14/71* | (2006.01) |
| *C07K 14/82* | (2006.01) |
| *C07K 16/32* | (2006.01) |
| *C12N 9/12* | (2006.01) |

(52) U.S. Cl.
CPC ............ *A61K 31/517* (2013.01); *A61P 35/00* (2018.01); *C07K 14/70596* (2013.01); *C07K 14/71* (2013.01); *C07K 14/82* (2013.01); *C07K 16/32* (2013.01); *C12N 9/12* (2013.01); *C12Y 207/10001* (2013.01)

(58) Field of Classification Search
CPC ....... A61K 31/517; A61P 35/00; C07K 14/71; C07K 14/82; C07K 16/32
See application file for complete search history.

(56) References Cited

U.S. PATENT DOCUMENTS

| | | | |
|---|---|---|---|
| 8,188,102 | B2 | 5/2012 | Lee et al. |
| 11,446,302 | B2 | 9/2022 | Robichaux et al. |
| 2002/0177601 | A1 | 11/2002 | Himmelsbach et al. |
| 2005/0085495 | A1 | 4/2005 | Soyka et al. |
| 2006/0178364 | A1 | 8/2006 | Jung et al. |
| 2007/0043009 | A1 | 2/2007 | Hennequin et al. |
| 2008/0286785 | A1 | 11/2008 | Nishio et al. |
| 2011/0142929 | A1 | 6/2011 | Messerschmid et al. |
| 2013/0071452 | A1* | 3/2013 | Kim ..................... C07D 401/12 |
| | | | 514/266.22 |
| 2013/0121996 | A1 | 5/2013 | Liu et al. |
| 2014/0112962 | A1 | 4/2014 | Kim et al. |
| 2015/0307947 | A1 | 10/2015 | Basu et al. |
| 2017/0343554 | A1 | 11/2017 | Sullivan et al. |
| 2018/0147279 | A1 | 5/2018 | Dar et al. |
| 2018/0333415 | A1 | 11/2018 | Potter et al. |
| 2019/0091229 | A1 | 3/2019 | Lichenstein et al. |
| 2020/0270351 | A1 | 8/2020 | Moores et al. |
| 2020/0299783 | A1 | 9/2020 | Wang et al. |
| 2020/0316071 | A1 | 10/2020 | Robichaux et al. |
| 2020/0370102 | A1 | 11/2020 | Park et al. |
| 2021/0235688 | A1 | 8/2021 | Tweardy et al. |
| 2021/0361655 | A1 | 11/2021 | Robichaux et al. |
| 2022/0041751 | A1 | 2/2022 | Heymach et al. |
| 2022/0089620 | A1 | 3/2022 | Muller et al. |
| 2022/0143023 | A1 | 5/2022 | Robichaux et al. |
| 2022/0143024 | A1 | 5/2022 | Andreeff et al. |
| 2022/0163532 | A1 | 5/2022 | Sood et al. |
| 2022/0175779 | A1 | 6/2022 | Robichaux et al. |
| 2022/0193074 | A1 | 6/2022 | Robichaux et al. |
| 2022/0202821 | A1 | 6/2022 | Tainer et al. |
| 2022/0305015 | A1 | 9/2022 | Hung et al. |

(Continued)

FOREIGN PATENT DOCUMENTS

| | | |
|---|---|---|
| CN | 109276717 A | 1/2019 |
| CN | 113271948 A | 8/2021 |
| EC | 03-4464 | 3/2003 |

(Continued)

OTHER PUBLICATIONS

Wen (J. Mol. Diagn. vol. 17 pp. 487-495 published 2015), (Year: 2015).*
Kim (Cancer Res Treat vol. 50 pp. 835-842. Published online Aug. 29, 2017). (Year: 2017).*
Lee (APMIS vol. 113 pp. 683-687 Published 2005). (Year: 2005).*
Nam (Cancer Letters vol. 302 pp. 155-165 published 2011) (Year: 2011).*
Lee (Clinical Cancer Research vol. 12 pp. 57-61 published 2006) (Year: 2006).*
Kavuri (Cancer Discovery vol. 5 pp. 832-841 published 2015). (Year: 2015).*

(Continued)

*Primary Examiner* — George W Kosturko

(74) *Attorney, Agent, or Firm* — pH IP Law

(57)     ABSTRACT

The present disclosure provides methods of treating cancer in a patient determined to have an HER2 exon 21 mutation by administering a third-generation tyrosine kinase inhibitor, such as poziotinib.

14 Claims, 23 Drawing Sheets

Specification includes a Sequence Listing.

(56) References Cited

U.S. PATENT DOCUMENTS

2022/0356467 A1    11/2022    Luthra et al.

FOREIGN PATENT DOCUMENTS

| | | |
|---|---|---|
| EC | 03-4646 | 7/2003 |
| EC | 06-6509 | 10/2006 |
| EC | 07-7645 | 8/2007 |
| EC | 10-10650 | 12/2010 |
| EC | 14-13121 | 2/2014 |
| JP | 2010-529115 A | 8/2010 |
| JP | 2014-513706 A | 6/2014 |
| JP | 2014-516082 A | 7/2014 |
| JP | 2020502059 A5 | 1/2021 |
| KR | 10-2016-0043114 A | 4/2016 |
| WO | WO 2002/018351 A1 | 3/2002 |
| WO | WO 2006/091899 A2 | 8/2006 |
| WO | WO 2008/150118 A2 | 12/2008 |
| WO | WO 2012/156437 A1 | 11/2012 |
| WO | WO 2012/169733 A1 | 12/2012 |
| WO | WO 2016/125169 A1 | 8/2016 |
| WO | WO 2017/067447 A1 | 4/2017 |
| WO | WO 2017/139468 A1 | 8/2017 |
| WO | WO 2017/198602 A1 | 11/2017 |
| WO | WO 2017/210214 A1 | 12/2017 |
| WO | WO 2018/094225 A1 | 5/2018 |
| WO | WO 2018/156812 A1 | 8/2018 |
| WO | WO 2019/191279 A1 | 10/2019 |
| WO | WO 2020/005932 A1 | 1/2020 |
| WO | WO 2020/005934 A1 | 1/2020 |
| WO | WO 2020/055643 A2 | 3/2020 |
| WO | WO 2020/132633 A1 | 6/2020 |
| WO | WO 2020/150208 A1 | 7/2020 |
| WO | WO 2020/205521 A1 | 10/2020 |
| WO | WO 2020/205632 A1 | 10/2020 |

OTHER PUBLICATIONS

Chen, Z. et al., "Non-small-cell lung cancers: a heterogeneous set of diseases," *Nat Rev Cancer*, 14.8 (2014): 535-546.

Frega, S. et al., "A Triple Rare E709K and L833V /H835L *EGFR* Mutation Responsive to an Irreversible Pan-HER Inhibitor: A Case Report of Lung Adenocarcinoma Treated with Afatinib," *Journal of Thoracic Oncology*, 11.5 (2016): e63-e66.

Heigener, D. F. et al., "Afatinib in Non-Small Cell Lung Cancer Harboring Uncommon *EGFR* Mutations Pretreated With Reversible EGFR Inhibitors," *The Oncologist*, 20 (2015): 1167-1174.

Hurwitz, J. L. et al., "Afatinib treatment in advanced non-small cell lung cancer," *Lung Cancer: Targets and Therapy*, 2 (2011): 47-57.

Inamura, K., "Lung Cancer: Understanding its Molecular Pathology and the 2015 WHO Classification," *Frontiers in Oncology*, 7 (2017): 193, 1-7.

Nagano, T et al., "Mechanism of Resistance to Epidermal Growth Factor Receptor-Tyrosine Kinase Inhibitors and a Potential Treatment Strategy," *Cells*, 7.212 (2018): 7110212, 1-16.

Schrock, A. B. et al., "Comprehensive Genomic Profiling Identifies Frequent Drug-Sensitive EGFR Exon 19 Deletions in NSCLC not Identified by Prior Molecular Testing," *Clinical Cancer Research*, 22.13 (2016): 3281-3285.

Shen, Y-C. et al., "Comparing the effects of afatinib with gefitinib or Erlotinib in patients with advanced-stage lung adenocarcinoma harboring non-classical epidermal growth factor receptor mutations," *Lung Cancer*, 110 (2017): 56-62.

Wang, W-L. et al., "Abstract 4018: Mutations of HER2 at L755 residue results in HER2 nuclear accumulation and enhances breast cancer stem cell activity," *AACR Annual Meeting*, vol. 78 (2018), 13 Supplement, 4018, 1-4.

Wu, J-Y et al., "Effectiveness of tyrosine kinase inhibitors on uncommon E709X epidermal growth factor receptor mutations in non-small-cell lung cancer," *OncoTargets and Therapy*, 9 (2016): 6137-6145.

Zeng, L. et al., "*EGFR* exon 18 DelE709_T710insD as an Acquired Resistance Mechanism to Afatinib in an Advanced *EGFR* exon 18 E709H Lung Adenocarcinoma," *Journal of Thoracic Oncology*, 13.6 (2018): e93-e107.

Castellano. G. M. et al., "A Novel Acquired Exon 20 *EGFR* M766QMutation in Lung Adenocarcinoma Mediates Osimertinib Resistance but is Sensitive to Neratinib and Poziotinib," *Journal of Thoracic Oncology*, 14.11 (2019): 1982-1988.

Hanker, A. B. et al., "An acquired HER2 T798I gatekeeper mutation induces resistance to neratinib in a patient with HER2 mutant-driven breast cancer," *Cancer Discover.*, 736 (2017): 575-585.

Koga, T. et al., "Activity of a novel HER2 inhibitor, poziotinib, for HER2 exon 20 mutations in lung cancer and mechanism of acquired resistance: An in vitro study," *Lung Cancer*, 126 (2018): 72-79.

Kumar, R. D. et al., "Analysis of somatic mutations across the kinome reveals loss-of-function mutations in multiple cancer types," *Scientific Reports*, 7 (2017): 6418, 1-12.

Le, X. et al., "Poziotinib in Non-Small-Cell Lung Cancer Harboring *HER2* Exon 20 Insertion Mutations After Prior Therapies: ZENITH20-2 Trial," *Journal of Clinical Oncology*, 40.7 (2022): 710-719.

Morimura, O. et al., "Trastuzumab emtansine suppresses the growth of HER2-positive small-cell lung cancer in preclinical models," *Biochemical and Biophysical Research Communications*, 488 (2017): 596-602.

Prelaj, A. et al., "Poziotinib for EGFR and HER2 exon 20 insertion mutation in advanced NSCLC: Results from the expanded access program," *European Journal of Cancer*, 149 (2021): 235-248.

Udagawa, H. et al., "Clinical Outcome of Non-Small Cell Lung Cancer with EGFR/HER2 Exon 20 Insertions Identified in the LC-SCRUM-Japan," *Journal of Thoracic Oncology*, 14.105 (2019): S224.

"AmoyDx™ EGFR 29 mutations detection kit," technical report by AmoyDx, Apr. 2012.

"A phase 1b study of poziotinib in combination with T-DM1 in women with advanced or metastatic HER2-positive breast cancer," Clinical study record, US National Library of Medicine, Feb. 12, 2018.

"A phase 2 study of poziotinib in patients with non-small cell lung cancer, locally advanced or metastatic, with EGFR or HER2 exon 20 insertion mutation (POZITIVE20-1)," Clinical study record, US National Library of Medicine, Oct. 24, 2017.

"Poziotinib in EGFR exon 20 mutant advanced NSCLC," Clinical Trial NCT03066206, Clinical study record, US National Library of Medicine, Feb. 28, 2017.

"A Study of Poziotinib in Combination with T-DM1 in HER2-Positive Breast Cancer," Clinical Trial NCT03429101, Clinical study record, submitted Apr. 30, 2018. (1).

"A Study of Poziotinib in Combination with T-DM1 in HER2-Positive Breast Cancer," Clinical Trial NCT03429101, Clinical study record, first posted Feb. 12, 2018. (2).

"Vizimpro® (dacomitinib) receives marketing authorization in European Union (EU) for the first-line treatment of adult patients with EGFR-mutated non-small cell lung cancer," Pfizer Inc., Apr. 2019.

An, S-.J et al., "Identification of Enriched Driver Gene Alterations in Subgroups of Non-Small Cell Lung Cancer Patients Based on Histology and Smoking Status," *PLOS ONE*, 7 (2012): 1-8, e40109.

Anido, J. et al., "ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells," *Clin Cancer Res*, 9 (2003): 1274-1283.

Arcila, M. E. et al., "EGFR Exon 20 Insertion Mutations in Lung Adenocarcinomas: Prevalence, Molecular Heterogeneity, and Clinicopathologic Characteristics," *Mol Cancer Ther.*, 12 (2013): 220-229.

Arcila, M. E. et al., "Prevalence, Clinicopathologic Associations, and Molecular Spectrum of ERBB2 (HER2) Tyrosine Kinase Mutations in Lung Adenocarcinomas," *Clin Cancer Res.*, 18 (2012): 4910-4918.

Baselga, J. et al., "Lapatinib with trashtuzumab for HER2-positive early breast cancer (NeoALTTO): a randomized, open-label, multicentre, phase 3 trial," *Lancet*, 379 (2012): 633-640.

(56)         References Cited

OTHER PUBLICATIONS

Besse, B. et al., "Neratinib (N) with or without Temsirolimus (TEM) in Patients (PTS) with Non-Small Cell Lung Cancer (NSCLC) carrying HER2 Somatic mutations: An International Randomized Phase II Study," *Annals of Oncology*, 25.Supplement 4 (2014): abstract.

Bose, R. et al., "Activating HER2 Mutations in HER2 Gene Amplification Negative Breast Cancer," *Cancer Discovery*, 3 (2013): 224-237.

Callegari, D. et al., "L718Q mutant EGFR escapes covalent inhibition by stabilizing a non-reactive conformation of the lung cancer drug Osimertinib," *Chem Sci*, 9 (2018): 2740-2749.

Cardona, A. F. et al., "EGFR exon 20 insertion in lung adenocarcinomas among Hispanics (geno1.2-CLICaP)," *Lung Cancer*, 125 (2018): 265-272.

Cha, M. Y. et al., "Antitumor activity of HM781-36B, a highly effective pan-HER inhibitor in erlotinib-resistant NSCLC and other EGFR-dependent cancer models," *International Journal of Cancer*, 130 (2012): 2445-2454.

Chan, A. et al., "Neratinib after trastusumab-based adjuvant therapy in patients with HER2-positive breast cancer (ExteNET): a multicentre, randomized, double-blind, placebo-controlled, phase 3 trial," *The Lancet Oncology*, 17.3 (2016): 367-377.

Cho, J. et al., "Cetuximab response of lung cancer-derived EGF receptor mutants is associated with asymmetric dimerization," *Cancer Res.*, 73 (2013): 6770-6779.

Costa, D. B. et al., "Pulse afatinib for *ERBB2* exon 20 insertion mutated lung Adenocarcinomas," *J Thorac Oncol.*, 11 (2016): 918-923.

Cretella, D. et al. "Trastuzumab emtansine is active on HER-2 overexpressing NSCLC cell lines and overcomes gefitinib resistance," *Molecular Cancer*, 13 (2014): 1-12.

De Greve, J. et al., "Clinical activity of afatinib (BIBW 2992) in patients with lung adenocarcinoma with mutations in the kinase domain of HER2/neu," *Lung Cancer*, 76.1 (2012): 123-127.

Elamin, Y. et al., "Preliminary Results of a Phase II Study of Poziotinib in EHFR Exon 20 Mutant Advanced NSCLC," *Journal of Thoracic Oncology*, 12 (2017): abstract.

English translation of Office Action issued in Ukrainian Patent Application No. a 2019 06706, dated Apr. 18, 2023.

English translation of First Office Action issued in Chinese Patent Application No. 201780083541.7, dated Aug. 29, 2022.

English translation of Second Office Action issued in Chinese Patent Application No. 201780083541.7, dated Apr. 13, 2023.

English Translation of First Office Action issued in Eurasian Patent Application No. 201991205, dated Jan. 26, 2021.

English Translation of Second Office Action issued in Eurasian Patent Application No. 201991205, dated Aug. 25, 2021.

English Translation of First Office Action issued in Korean Patent Application No. 10-2019-7017346, dated Oct. 31, 2022.

English Translation of Second Office Action issued in Korean Patent Application No. 10-2019-7017346, dated Mar. 20, 2023.

English Translation of First Office Action issued in Korean Patent Application No. 10-2023-7033201, dated Dec. 8, 2023.

English translation of First Office Action issued in Mexican Patent Application No. MX/a/2019/005824, dated May 20, 2021.

English translation of Second Office Action issued in Mexican Patent Application No. MX/a/2019/005824, dated Jan. 19, 2022.

English translation of Office Action issued in Taiwanese Patent Application No. 106139967, dated Feb. 21, 2022.

English Translation of First Office Action issued in Japanese Patent Application No. 2019-526282, dated Dec. 8, 2021.

English Translation of Second Office Action issued in Japanese Patent Application No. 2019-526282, dated Sep. 1, 2022.

English Translation of First Office Action issued in Japanese Patent Application No. 2023-067134, dated Apr. 9, 2024.

English Translation of First Office Action issued in Chinese Patent Application No. 2020800387910, dated Jun. 30, 2023.

English Translation of Second Office Action issued in Chinese Patent Application No. 2020800387910, dated Dec. 28, 2023.

English Translation of Third Office Action issued in Chinese Patent Application No. 2020800387910, dated May 31, 2024.

English Translation of First Office Action issued in Japanese Patent Application No. 2021-557927, dated Mar. 25, 2024.

English Translation of First Office Action issued in Chinese Patent Application No. 2020800323406, dated Oct. 23, 2023.

English Translation of Second Office Action issued in Chinese Patent Application No. 2020800323406, dated May 1, 2024.

English Translation of First Office Action issued in Japanese Patent Application No. 2021-557941, dated May 2, 2024.

English Translation of First Office Action issued in Chinese Patent Application No. 202080044361X, dated Jan. 12, 2024.

English Translation of First Office Action issued in Japanese Patent Application No. 2021-561673, dated May 9, 2024.

English Translation of First Office Action issued in Chinese Patent Application No. 202080032255X, dated Jul. 15, 2023.

English Translation of Second Office Action issued in Chinese Patent Application No. 202080032255X, dated Mar. 9, 2024.

English Translation of First Office Action issued in Japanese Patent Application No. 2021-561677, dated Apr. 8, 2024.

Ettinger, D. S. et al., "NCCN Guidelines Insights: Non-Small Cell Lung Cancer, Version 5.2018," *J Natl Compr Canc Netw.*, 16.7 (2018): 807-821.

Extended European Search Report issued in European Patent Application No. 17871141.2, dated Aug. 31, 2020.

Extended European Search Report issued in European Patent Application No. 20783802.0, dated Mar. 31, 2023.

Extended European Search Report issued in European Patent Application No. 19775368.4, dated Feb. 23, 2022.

Extended European Search Report issued in European Application No. 19899260.4, mailed Nov. 24, 2022.

Extended European Search Report issued in European Patent Application No. 20782979.7, dated Dec. 6, 2022.

Extended European Search Report issued in European Application No. 20792247.7, mailed Jan. 4, 2023.

Extended European Search Report issued in European Application No. 20790528.2, mailed May 4, 2023.

Fassunke, J. et al., Overcoming EGFR(G724S)-mediated osimertinib resistance through unique binding characteristics of second-generation EGFR inhibitors. *Nature Communications*, 9 (2018): 4655, 1-14.

Gan, H. K. et al., "The epidermal growth factor receptor (EGFR) tyrosine kinase inhibitor AG1478 increases the formation of inactive untethered EGFR dimers. Implications for combination therapy with monoclonal antiboy," *J Bio chem.*, 282 (2007): 2840-2850.

Gonzalvez, F. et al., Abstract 2644: AP32788, a potent, selective inhibitor of EGFR and HER2 oncogenic mutants, including exon 20 insertions, in preclinical models, *Cancer Res.*, 76.14 Supplemental (2016): 1-2.

Greulich, H. et al., "Functional analysis of receptor tyrosine kinase mutations in lung cancer identifies oncogenic extracellular domain mutations of ERBB2," *Proc Natl Acad Sci U S A*, 109.36 (2012): 14476-14481.

Han, J-Y. et al., "A Phase II Study of Poziotinib in Patients with Epidermal Growth Factor Receptor (EGFR)-Mutant Lung Adenocarcinoma Who Have Acquired Resistance to EGFR-Tyrosine Kinase Inhibitors," *Cancer Res Treat.*, 49 (2017): 10-19.

Heymach, J. et al., "A phase II trial of poziotinib in EGFR and HER2 exon 20 mutant non-small cell lung cancer (NSCLC)," *J Thorac Oncol.*, 13 (2018): S323-S324.

Hirano, T. et al., "In Vitro modeling to determine mutation specificity of EGFR tyrosine kinase inhibitors against clinically relevant *EGFR* mutants in non-small-cell lung cancer," *Oncotarget*, 6 (2015): 38789-38803.

Hyman, D. M. et al., "HER kinase inhibition in patients with HER2- and HER3-mutant cancers," *Nature*, 554.7691 (2018): 189-194.

Kamitani, H. et al., "Mutations in transmembrane domain of carbB-2 gene in human malignant tumours of the central nervous system," *Neurological Research*, 14.3 (1992): 236-240.

Kim, E. et al., "Metabolite identification of a new tyrosine kinase inhibitor, HM781-36B, and a pharmacokinetic study by liquid chromatography/tandem mass spectrometry," *Rapid Communications in Mass Spectrometry*, 27.11 (2013): 1183-1195.

(56)                    References Cited

OTHER PUBLICATIONS

Kim, D. W. et al., "Phase I study of HM781-36B, an irreversible pan-HER tyrosine kinase inhibitor (TKI) in patients with advanced solid tumor and the therapeutic potential in patients with advanced non-small cell lung cancer (NSCLC)", Abstract #2029, Department of Internal Medicine, Seoul National University Hospital Seoul/Korea (2013).

Kim, T. M. et al., "Phase 1 studies of Poziotinib, an irreversible Pan-HER tyrosine kinase inhibitor in patients with advanced solid tumors," *Cancer Res Treat.*, 50.3 (2018): 835-842.

Kobayashi, Y. et al., "EGFR exon 18 mutations in lung cancer: molecular predictors of augmented sensitivity to afatinib or neratinib as compared with first- or third-generation TKIs," *Clinical Cancer Research*, 21.23 (2015): 5305-5313.

Kobayashi, Y. et al., "Not all epidermal growth factor receptor mutations in lung cancer are created equal: Perspectives for individualized treatment strategy," *Cancer Science*, 107 (2016): 1179-1186.

Kosaka, T. et al., "Response Heterogeneity of EGFR and HER2 Exon 20 Insertions to Covalent EGFR and HER2 Inhibitors," *Cancer Res*, 77 (2017): 2712-2721.

Kris, M. G. et al., "Targeting HER2 aberrations as actionable drivers in lung cancers: phase II trial of the pan-HER tyrosine kinase inhibitor dacomitinib in patients with HER2-mutant or amplified tumors," *Ann Oncol*, 26.7 (2015): 1421-1427.

Le, X. et al., "Landscape of EGFR-dependent and -independent resistance mechanisms to osimertinib and continuation therapy post-progression in EGFR-mutant NSCLC," *Clin Cancer Res*, 24 (2018): 6195-6203.

Lee, K. Y. et al., "Molecular Diagnosis in Lung Cancer," *J Lung Cancer*, 9 (2010): 9-14.

Li, B. T. et al., "Ado-trastuzumab emtansine for patients with HER2-mutant lung cancers: results from a phase II basket trial," *J Clin Oncol*, 36 (2018): 2532-2537.

Lynch, T. J. et al., "Activating mutations in the epidermal growth factor receptor underlying responsiveness of non-small-cell lung cancer to gefitinib," *N Engl J Med*, 350.2 (2004): 2129-2139.

Maemondo, M. et al., "Gefitinib or Chemotherapy for Non-Small-Cell Lung Cancer with Mutated EGFR," *N Engl J Med*, 362 (2010): 2380-2388.

Mazieres, J. et al., "Lung Cancer that harbors an *HER2* mutation: epidemiologic characteristics and therapeutic perspectives," *Journal of Clinical Oncology*, 31 (2013): 1997-2003.

Mazieres, J. et al., "Lung cancer patients with HER2 mutations treated with chemotherapy and HER2-targeted drugs: results from the European EUHER2 cohort," *Annals of Oncology*, 27 (2016): 281-286.

Mazieres, J. et al., "Crizotinib therapy for advanced lung adenocarcinoma and a ROS1 rearrangement: results from the EUROS1 cohort," *J Clin Oncol*, 33.9 (2015): 992-999.

Mehta, R. et al., "The Role of HER2 Testing in Advanced Colorectal Cancer," *Current Colorectal Cancer Reports*, 14 (2018): 184-191.

Meric-Bernstam, F. et al., "Advances in HER2-Targeted Therapy: Novel Agents and Opportunities Beyond Breast and Gastric Cancer," *Clinical Cancer Research*, 25.7 (2019): 2033-2041.

Mitsudomi, T. et al., "Mutations of the epidermal growth factor receptor gene and related genes as determinants of epidermal growth factor receptor tyrosine kinase inhibitors sensitivity in lung cancer," *Cancer Sci*, 98.12 (2007): 1817-1824.

Mitsudomi, T. et al., "Commentary on EGFR gene mutation examination in lung cancer patients," *EGFR commentary committee of the Japan Lung Cancer Society*, 1 (2009): i-xviii.

Nagano, M. et al., "High-Throughput Functional Evaluation of Variants of Unknown Significance in ERBB2," *Clin Cancer Res*, 24.20 (2018): 5112-5122.

Nam, H-J. et al., "Antitumor activity of HM781-36B, an irreversible Pan-HER inhibitor, alone or in combination with cytotoxic chemotherapeutic agents in gastric cancer," *Cancer Lett.*, 302 (2011): 155-165.

Notice of Allowance issued in Eurasian Patent Application No. 201991205, dated Apr. 22, 2022.

Notice of Allowance issued in Korean Patent Application No. 10-2019-7017346, dated Jun. 27, 2023.

First Office Action issued in Indonesian Patent Application No. P00201904953, dated Mar. 19, 2021.

Second Office Action issued in Indonesian Patent Application No. P00201904953, dated Mar. 31, 2023.

Office Action issued in Chilean Office Action 2019-001353, mailed Apr. 20, 2021.

Office Action issued in Chilean Office Action 2019-001353, mailed Dec. 1, 2023.

Office Action issued in Australian Patent Application No. 2017363199, dated Aug. 17, 2022.

Office Action issued in Brazilian Patent Application No. 11 2019 010020-2, dated Oct. 4, 2022.

Office Action issued in Columbian Patent Application No. NC2019/0006218, dated Jul. 29, 2022.

Office Action issued in Thai Patent Application No. 1901002990, dated Apr. 26, 2024.

Office Action issued in Egyptian Patent Application No. PCT 1533/2021, dated Jul. 18, 2022.

Office Action issued in Russian Patent Application No. 2021131360, mailed Dec. 7, 2021.

Office Action issued in European Patent Application No. 17871141.2, dated Jun. 26, 2023.

Office Action issued in U.S. Appl. No. 17/042,012, dated May 20, 2024.

Office Action issued in Japanese Application No. 2020-551912, mailed Jan. 30, 2023, and English translation thereof.

Office Action issued in Chinese Application No. 201980022143.3, mailed Feb. 22, 2023, and English translation thereof.

Office Action issued in Canadian Patent Application No. 3,121,807, dated Oct. 19, 2023.

Office Action issued in Chinese Patent Application No. 2019800871408, dated Jun. 22, 2023.

Office Action issued in Japanese Patent Application No. 2021-535545, dated Dec. 5, 2023.

Opposition filed in Ecuadoran Application No. 2019-43254, dated Feb. 5, 2020 (English translation).

Ou, S-H. I. et al., "HER2 Transmembrane Domain (TMD) Mutations (V659/G660) That Stabilize Homo- and Heterodimerization are Rare Oncogenic Drivers in Lung Adenocarcinoma That Respond to Afatinib," *Journal of Thoracic Oncology*, 12.3, (2017): 446-457.

Pan, Y. et al., "Prevalence, Clinicopathologic Characteristics, and Molecular Associations of EGFR Exon 20 Insertion Mutations in East Asian Patients with Lung Adenocarcinoma," *Annals of Surgical Oncology*, 21 (2014): S490-S496.

Paez, J. G. et al., "EGFR mutations in lung cancer: correlation with clinical response to gefitinib therapy," *Science*, 304.5676 (2004): 1497-1500.

Papadimitrakopoulou, V. A. et al., "Everolimus and Erlotinib as Second- or Third-Line Therapy in Patients with Advanced Non-Small-Cell Lung Cancer," *Journal of Thoracic Oncology*, 7 (2012): 1594-1601.

Park, Y. H. et al., "A phase II trial of pan-HER inhibitor Poziotinib, in patients with HER2-positive metastatic breast cancer who have received at least two prior HER2-directed regimens: The results of Nov120101-203 trial," *International Journal of Cancer*, 143 (2018): 3240-3247.

Pao, W. et al., "EGF receptor gene mutations are common in lung cancers from "never smokers" and are associated with sensitivity of tumors to gefitinib and erlotinib," *Proc Natl Acad Sci USA*, 7.101 (2004): 13306-13311.

Partial Supplementary European Search Report issued in European Application No. 17871141.2, mailed May 29, 2020.

Partial Supplementary European Search Report issued in European Application No. 19775368.4, mailed Nov. 22, 2021.

PCT International Preliminary Report on Patentability issued in International Patent Application No. PCT/US2020/025228, mailed Oct. 14, 2021.

(56) References Cited

OTHER PUBLICATIONS

PCT International Search Report and Written Opinion issued in International Patent Application No. PCT/US2020/025228, mailed Jul. 22, 2020.
PCT International Preliminary Report on Patentability issued in International Patent Application No. PCT/US2017/062326, mailed May 31, 2019.
PCT International Search Report and Written Opinion issued in International Patent Application No. PCT/US2017/062326, mailed Mar. 29, 2018.
PCT International Preliminary Report on Patentability for PCT/US2019/024353 dated Sep. 29, 2020, 14 pages.
PCT International Search Report and Written Opinion for PCT/US2019/024353 dated Oct. 1, 2019, 20 pages.
PCT International Search Report and Written Opinion issued in International Application No. PCT/US2019/068153, mailed Apr. 14, 2020.
PCT International Preliminary Report on Patentability issued in International Application No. PCT/US2019/068153, mailed Jul. 1, 2021.
PCT International Search Report and Written Opinion issued in International Patent Application No. PCT/US2020/025478, mailed Aug. 27, 2020.
PCT International Preliminary Report on Patentability issued in International Patent Application No. PCT/US2020/025478, mailed Oct. 14, 2021.
PCT International Preliminary Report on Patentability issued in International Application No. PCT/US2020/028540, mailed Oct. 28, 2021.
PCT International Search Report and Written Opinion issued in International Application No. PCT/US2020/028540, mailed Jul. 8, 2020.
PCT International Preliminary Report on Patentability issued in International Application No. PCT/US2020/028547, mailed Oct. 28, 2021.
PCT International Search Report issued in International Application No. PCT/US2020/028547, mailed Jul. 22, 2020.
Perera, S. A. et al., "HER2$^{YVMA}$ Drives Rapid Development of Adenosquamous Lung Tumors in Mice That are Sensitive to BIBW2992 and Rapamycin Combination Therapy," Proc Natl Acad Sci U S A, 106 (2009): 474-479.
Riess, J. W. et al., "Diverse EGFR Exon 20 Insertions and Co-Occurring Molecular Alterations Identified by Comprehensive Genomic Profiling of NSCLC," Journal of Thoracic Oncology, 13.10 (2018): 1560-1568.
Robichaux, J. P. et al., "Inhibition of HER2 mutant non-small cell lung cancer using 3rd generation EGFR/HER2 inhibitors," Cancer Res, 76 (2016) (14 Supplement): 4799.
Robichaux, J. et al., "MA16.07 Drug Repurposing to Overcome De Novo Resistance of Non-Traditional EGFR Mutations," Journal of Thoracic Oncology, 12 (2017): S438.
Robichaux, J. P. et al., "Mechanisms and clinical activity of an EGFR and HER2 exon 20-selective kinase inhibitor in non-small cell lung cancer," Nat Med., 24.5 (2018): 638-646.
Robichaux, J. P. et al., "Pan-Cancer Landscape and Analysis of ERBB2 Mutations Identifies Poziotinib as a Clinically Active Inhibitor and Enhancer of T-DM1 Activity", Cancel Cell, 36.4 (2019): 444-457.
Russo, A. et al., "Heterogeneous Responses to Epidermal Growth Factor Receptor (EGFR) Tyrosine Kinase Inhibitors (TKIs) in Patients with Uncommon EGFR Mutations: New Insights and Future Perspectives in this Complex Clinical Scenario," International Journal of Molecular Sciences, 20 (2019): 1431, 1-20.
Scaltriti, M. et al., "Lapatinib, a HER2 tyrosine kinase inhibitor, induces stabilization and accumulation of HER2 and potentiates trastuzumab-dependent cell cytotoxicity," Oncogene, 28 (2009): 803-814.
Search Report issued in Singapore Patent Application No. 11202009498R, mailed Jun. 29, 2022.

Search Report issued in Singapore Patent Application No. 11202109531U, issued Jul. 20, 2023.
Search Report issued in Singapore Patent Application No. 11202111120V, issued Aug. 22, 2023.
Soria, J. C. et al., "Osimertinib in Untreated EGFR-Mutated Advanced Non-Small-Cell Lung Cancer," N Engl J Med, 378.2 (2018): 113-125.
Sun, Z. et al., "Analysis of different HER-2 mutations in breast cancer progression and drug resistance," J. Cell. Mol. Med., 19.12 (2015): 2691-2701.
Suzawa, K. et al., "Antitumor effect of afatinib, as a human epidermal growth factor receptor 2-targeted therapy, in lung cancers harboring HER2 oncogene alterations," Cancer Science, 107 (2016): 45-52.
Thress, K. S. et al., "Acquired EGFR C797S mutation mediates resistance to AZD9291 in non-small cell lung cancer harboring EGFR T790M," Nat Med., 21 (2015): 560-562.
Van Der Steen, N. et al., "Resistance to epidermal growth factor receptor inhibition in non-small cell lung cancer," Cancer Drug Resistance, 1 (2018): 230-249.
Vogel, C. L. et al., "Efficacy and safety of trastuzumab as a single agent in first-line treatment of HER2-overexpressing metastatic breast cancer," J Clin Oncol., 20.3 (2002): 719-726.
Vyse, S. et al., "Targeting EGFR exon 20 insertion mutations in non-small cell lung cancer," Signal Transduction and Targeted Therapy, 4.1(2019): 1-10.
Wang, S. E. et al., "HER2 kinase domain mutation results in constitutive phosphorylation and activation of HER2 and EGFR and resistance to EGFR tyrosine kinase inhibitors," Cancer Cell, 10.1 (2006): 25-38.
Wen, W. et al., "Mutations in the Kinase Domain of the HER2/ERBB2 Gene Identified in a Wide Variety of Human Cancers," The Journal of Molecular Diagnostics, 17 (2015): 487-495.
Woo, H. S. et al., "Epidermal growth factor receptor (EGFR) exon 20 mutations in non-small-cell lung cancer and resistance to EGFR-tyrosine kinase inhibitors," Investigational New Drugs, 32 (2014): 1311-1315.
Xu, Z.-q. et al., "Efficacy and safety of lapatinib and trustuzumab for HER2-positive breast cancer: a systematic review and meta-analysis of randomized controlled trials," BMJ Open, 7 (2017): e013053, 1-9.
Yamada, et al., "Mechanism of tumor resistance to EGFR-targeted therapies," Nippon Rinsho, 71 (2013): 258-262.
Yang, C-Y. et al., "Programmed cell death-ligand 1 expression is associated with a favourable immune microenvironment and better overall survival in stage I pulmonary squamous cell carcinoma," Eur J Cancer, 57 (2016): 91-103.
Yang, B. et al., "Atomistic insights into the lung cancer-associated L755P mutation in HER2 resistance to lapatinib: a molecular dynamics study," J. Mol Model, 21:24 (2015): 1-12.
Yang et al. "Clinical activity of afatinib in patients with advanced non-small-cell lung cancer harbouring uncommon EGFR mutations: a combined post-hoc analysis of LUX-Lung 2, LUX-Lung 3, and LUX-Lung 6," The Lancet Oncology, 16 (2015): 830-838.
Yang, M. et al., "NSCLC harboring EGFR exon-20 insertions after the regulatory C-helix of kinase domain responds poorly to known EGFR inhibitors," Int. J. Cancer, 139 (2016): 171-176.
Yasuda, H. et al., "EGFR exon 20 insertion mutations in non-small-cell lung cancer: preclinical data and clinical implications," Lancet Oncol, 13 (2012): e23-31.
Yasuda, H. et al., "Structural, biochemical and clinical characterization of epidermal growth factor receptor (EGFR) exon 20 insertion mutations in lung cancer," Sci Transl Med, 5 (2013): 1-23.
Yonesaka, K. et al., "An HER3-targeting antibody-drug conjugate incorporating a DNA topoisomerase I inhibitor U3-1402 conquers EGFR tyrosine kinase inhibitor-resistant NSCLC," Oncogene, 38 (2019): 1398-1409.
Yu, X. et al., "First-generation EGFR tyrosine kinase inhibitor therapy in 106 patients with compound EGFR-mutated lung cancer: a single institution's clinical practice experience," Cancer Communication, 38 (2018): 1-13. C160.

(56)                  References Cited

OTHER PUBLICATIONS

Bianco. R. et al., "Inhibition of mTOR pathway by everolimus cooperates with EGFR inhibitors in human tumours sensitive and resistant to anti-EGFR drugs," *British Journal of Cancer*, 98 (2008): 923-930.

Herter-Sprie, G. S. et al., "Activating mutations in *ERBB2* and their impact on diagnostics and treatment," *Frontiers in Oncology*, 3.86 (2013): 1-10.

Kohsaka, S. et al., "A method of high-throughput functional evaluation of *EGFR* gene variants of unknown significance in cancer," *Sci. Transl. Med.*, 9 (2017): eaan6566, 1-12.

Liu, Y. et al., "Acquired *EGFR* L718V mutation mediates resistance to osimertinib in non-small cell lung cancer but retains sensitivity to afatinib," *Lung Cancer*, 118 (2018): 1-5.

Lu, S. et al., "*EGFR* and *ERBB2* Germline Mutations in Chinese Lung Cancer Patients and Their Roles in Genetic Susceptibility to Cancer," *Journal of Thoracic Oncology*, 14.4 (2019): 732-736.

Nishino, M. et al., "Effects of secondary *EGFR* mutations on resistance against upfront osimertinib in cells with *EGFR*-activating mutations in vitro," *Lung Cancer*, 126 (2018): 149-155.

\* cited by examiner

A

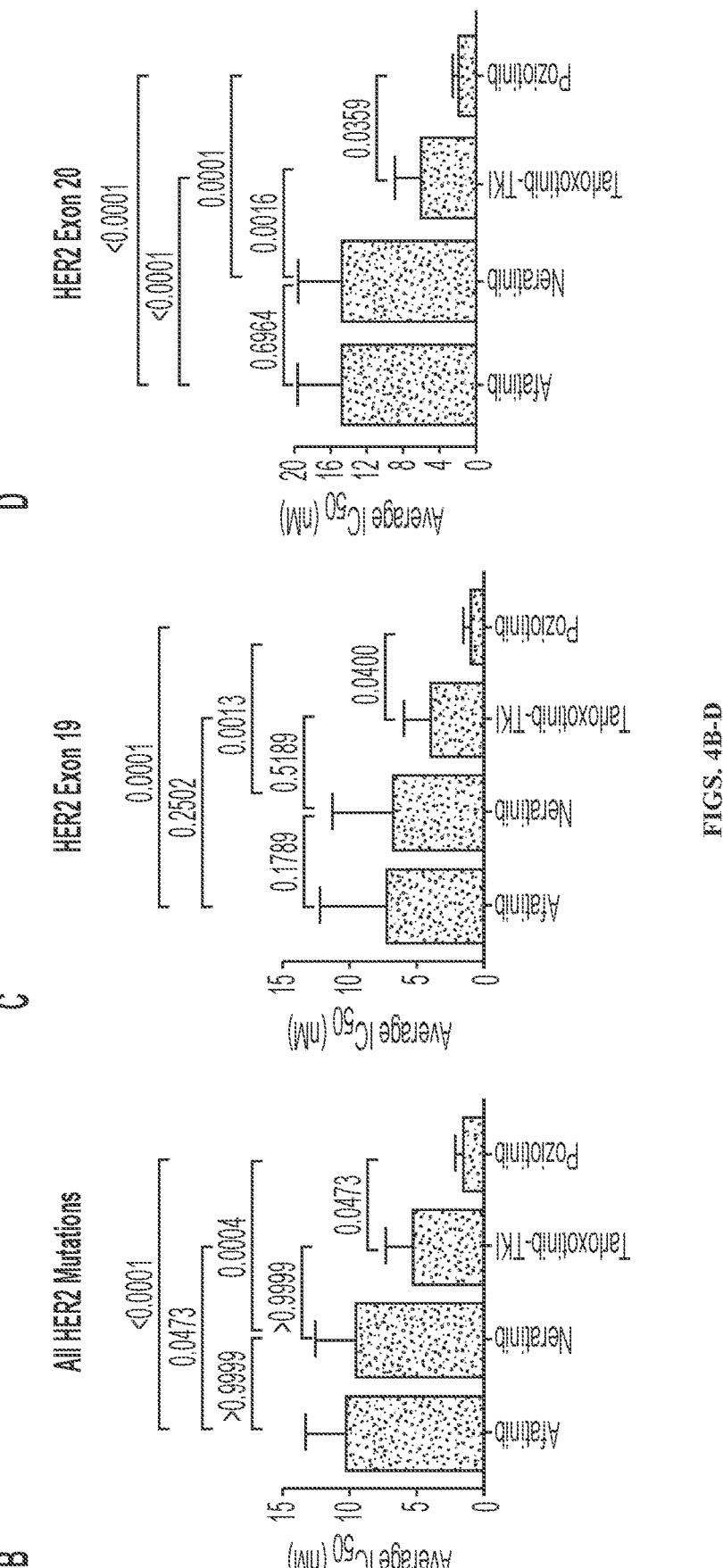
FIGS. 4B-D

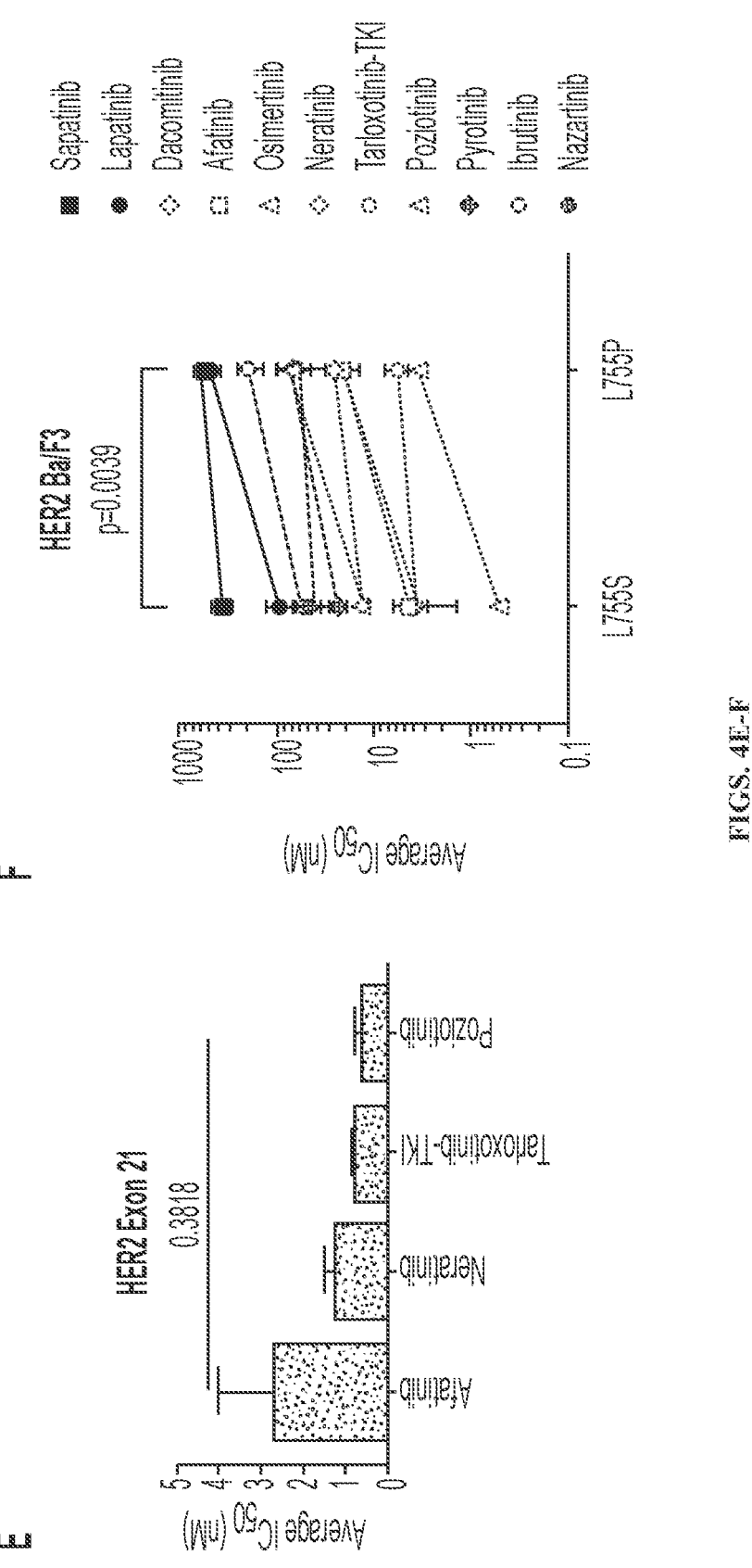
FIGS. 4E-F

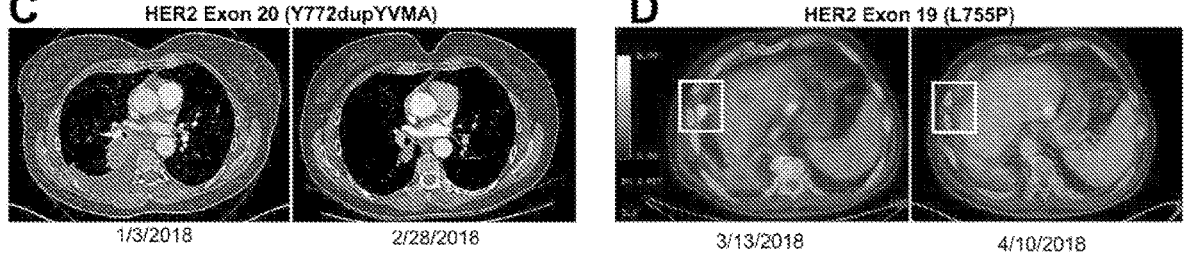
FIGS. 7C-D

A

B

C

D

F

| Number of mice bearing tumor (%) | | | | |
|---|---|---|---|---|
| | Vehicle | Poziotinib | T-DM1 | Poziotinib + T-DM1 |
| Day 15 | 9/9 (100%) | 12/12 (100%) | 7/9 (78%) | 0/20 (0%) |
| Day 45 | N/A | 12/12 (100%) | 9/9 (100%) | 6/20 (30%) |

G

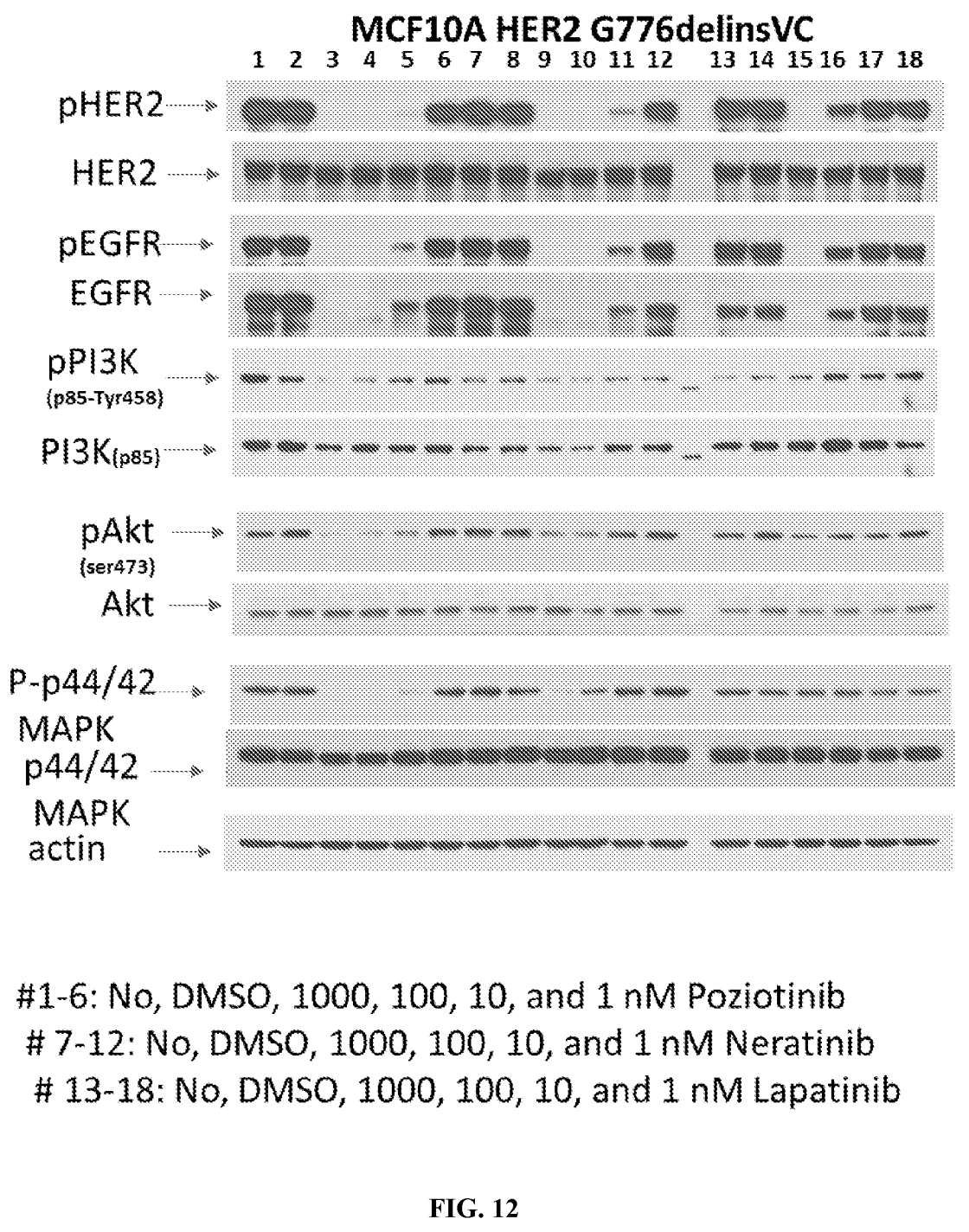

MCF10A HER2 G776delinsVC
1  2  3  4  5  6  7  8  9  10 11 12  13 14 15 16 17 18 pHER2

HER2 pEGFR

EGFR pPI3K
(p85-Tyr458)

PI3K(p85)

pAkt
(ser473)

Akt

P-p44/42
MAPK p44/42
MAPK actin

1-6: No, DMSO, 1000, 100, 10, and 1 nM Poziotinib
7-12: No, DMSO, 1000, 100, 10, and 1 nM Neratinib
13-18: No, DMSO, 1000, 100, 10, and 1 nM Lapatinib

FIG. 12

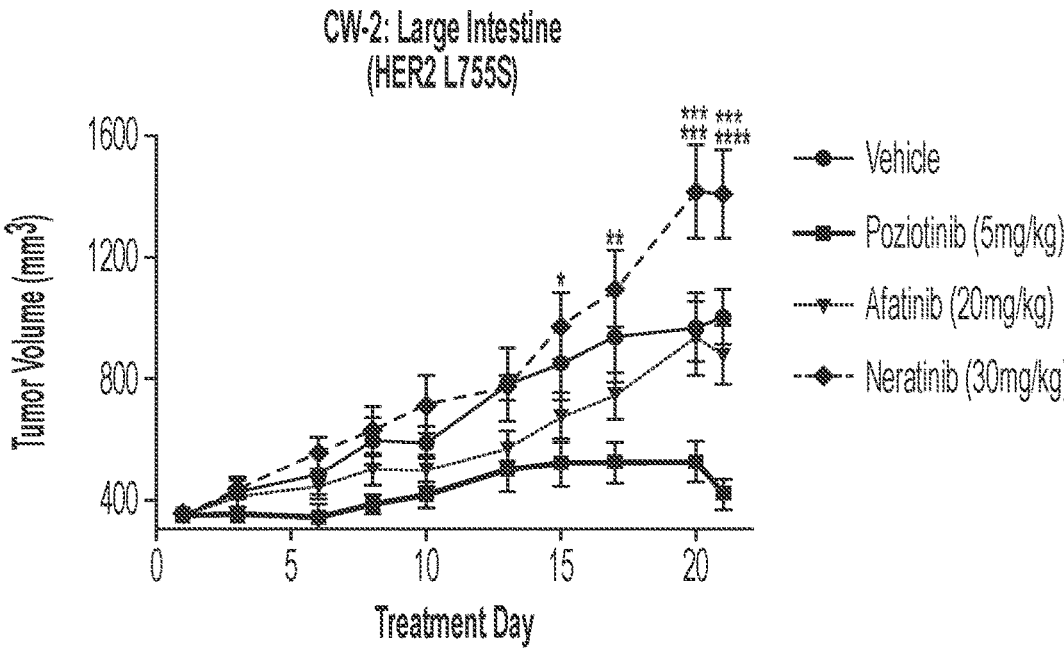

| Tukey's multiple comparisons test | Summary | Adjusted P Value |
|---|---|---|
| Day 10 | | |
| Vehicle vs. Poziotinib (5mg/kg) | ns | 0.3888 |
| Vehicle vs. Afatinib (20mg/kg) | ns | 0.8492 |
| Vehicle vs. Neratinib (30mg/kg) | ns | 0.6826 |
| Poziotinib (5mg/kg) vs. Afatinib (20mg/kg) | ns | 0.8809 |
| Poziotinib (5mg/kg) vs. Neratinib (30mg/kg) | * | 0.0333 |
| Afatinib (20mg/kg) vs. Neratinib (30mg/kg) | ns | 0.2222 |
| | | |
| Day 13 | | |
| Vehicle vs. Poziotinib (5mg/kg) | ns | 0.057 |
| Vehicle vs. Afatinib (20mg/kg) | ns | 0.2563 |
| Vehicle vs. Neratinib (30mg/kg) | ns | 0.9996 |
| Poziotinib (5mg/kg) vs. Afatinib (20mg/kg) | ns | 0.9266 |
| Poziotinib (5mg/kg) vs. Neratinib (30mg/kg) | ns | 0.0737 |
| Afatinib (20mg/kg) vs. Neratinib (30mg/kg) | ns | 0.3041 |

FIG. 13

| Day 15 | | |
|---|---|---|
| Vehicle vs. Poziotinib (5mg/kg) | * | 0.0152 |
| Vehicle vs. Afatinib (20mg/kg) | ns | 0.391 |
| Vehicle vs. Neratinib (30mg/kg) | ns | 0.7201 |
| Poziotinib (5mg/kg) vs. Afatinib (20mg/kg) | ns | 0.5209 |
| Poziotinib (5mg/kg) vs. Neratinib (30mg/kg) | *** | 0.0003 |
| Afatinib (20mg/kg) vs. Neratinib (30mg/kg) | * | 0.0452 |
| Day 17 | | |
| Vehicle vs. Poziotinib (5mg/kg) | ** | 0.0012 |
| Vehicle vs. Afatinib (20mg/kg) | ns | 0.3219 |
| Vehicle vs. Neratinib (30mg/kg) | ns | 0.5028 |
| Poziotinib (5mg/kg) vs. Afatinib (20mg/kg) | ns | 0.193 |
| Poziotinib (5mg/kg) vs. Neratinib (30mg/kg) | **** | <0.0001 |
| Afatinib (20mg/kg) vs. Neratinib (30mg/kg) | * | 0.0118 |
| Day 20 | | |
| Vehicle vs. Poziotinib (5mg/kg) | *** | 0.0005 |
| Vehicle vs. Afatinib (20mg/kg) | ns | 0.9896 |
| Vehicle vs. Neratinib (30mg/kg) | *** | 0.0007 |
| Poziotinib (5mg/kg) vs. Afatinib (20mg/kg) | ** | 0.0015 |
| Poziotinib (5mg/kg) vs. Neratinib (30mg/kg) | **** | <0.0001 |
| Afatinib (20mg/kg) vs. Neratinib (30mg/kg) | *** | 0.0002 |
| Day 21 | | |
| Vehicle vs. Poziotinib (5mg/kg) | **** | <0.0001 |
| Vehicle vs. Afatinib (20mg/kg) | ns | 0.6886 |
| Vehicle vs. Neratinib (30mg/kg) | ** | 0.0029 |
| Poziotinib (5mg/kg) vs. Afatinib (20mg/kg) | *** | 0.0003 |
| Poziotinib (5mg/kg) vs. Neratinib (30mg/kg) | **** | <0.0001 |
| Afatinib (20mg/kg) vs. Neratinib (30mg/kg) | **** | <0.0001 |

FIG. 13
CONTINUED

COMPOUNDS WITH ANTI-TUMOR ACTIVITY AGAINST CANCER CELLS BEARING HER2 EXON 21 INSERTIONS

This application is a national phase application under 35 U.S.C. § 371 of International Application No. PCT/US2020/025478, filed Mar. 27, 2020, which claims the benefit of U.S. Provisional Patent Application No. 62/826,758, filed Mar. 29, 2019, the entirety of each of which is incorporated herein by reference.

This invention was made with government support under grant number CA190628 awarded by the National Institutes of Health. The government has certain rights in the invention.

BACKGROUND

1. Field

The present invention relates generally to the field of molecular biology and medicine. More particularly, it concerns methods of treating patients with HER2 exon 21 mutations.

2. Description of Related Art

Erb-b2 receptor tyrosine kinase 2 (ERBB2) also known as human epidermal growth factor receptor 2 (HER2) amplifications occur in many cancer types and targeted agents such as trastuzumab, pertuzumab, trastuzumab emtansine (T-DM1), lapatinib, and neratinib have been shown to improve clinical outcomes compared to chemotherapy alone (Vogel et al., 2002). Activating mutations of ERBB2 (HER2) have been reported in many cancer types (Kris et al., 2015). While FDA-approved targeted therapies exist for cancers harboring HER2 amplifications, there are no approved targeted therapies specifically for HER2 mutations. However, National Comprehensive Cancer Network non-small cell lung cancer (NSCLC) guidelines recommend testing newly diagnosed patients with broad molecular profiling to detect HER2 mutations (Ettinger et al., 2018).

Recent clinical studies of targeted agents for HER2 mutant cancers have focused on covalent second-generation tyrosine kinase inhibitors (TKIs) such as afatinib, neratinib, and dacomitinib. The SUMMIT pan-cancer study reported that patients receiving neratinib had an objective response rate (ORR) of less than 15% for all HER2 mutations (Hyman et al., 2018). However, across multiple studies, when patients were stratified by cancer type, patients with breast cancer have had ORRs of 12.5%-32% to single agent neratinib (Hyman et al., 2018; Ma et al., 2017); whereas patients with lung cancer had 0%-4% response rates to neratinib as a single agent (Hyman et al., 2018; Mazieres et al., 2015), demonstrating cancer-specific differences in efficacy of HER2 inhibition. Interestingly, within a single cancer type, HER2 targeting agents appear to elicit variant-specific differences. In the SUMMIT trial, patients with HER2 kinase domain point mutations had an ORR of 21.4%, whereas patients with exon 20 insertions had an ORR of 7.1% to neratinib (Hyman et al., 2018). Furthermore, dacomitinib had an ORR of 11.5% for HER2 mutant NSCLC, but no responses occurred among patients bearing the HER2 exon 20 insertion mutation, p.Y772dupYVMA (Kris et al., 2015), and in two separate studies of afatinib, patients with exon 20 insertion positive NSCLC had response rates of 18.2% and 18.8% to afatinib.

Studies of HER2 monoclonal antibodies and drug-antibody conjugates revealed similar results. The pan-cancer study MyPathway tested the efficacy of the combination of anti-HER2 monoclonal antibodies trastuzumab and pertuzumab in 35 different tumor types and reported an ORR of 11% for all HER2 mutations and cancer types. In this study, only 21% of NSCLC patients and one biliary cancer patient responded among the 35 tumor types included. In addition, in a pan-HER2 mutant NSCLC study testing the efficacy of T-DM1, patients harboring exon 20 insertion mutations had an ORR of 54.5%, but patients with exon 19 mutations did not have partial responses. These cancer-specific and variant-specific differences in patient outcomes demonstrate the unmet need for a detailed and systematic understanding of the landscape of HER2 mutations across cancer types and the identification of effective therapies for the various HER2 mutations identified.

Pre-clinical studies of HER2 activating mutations have also reported differential sensitivity to various TKIs. Studies of mutations within the HER2 extracellular domain have shown that these mutations are associated with resistance to non-covalent inhibitors such as lapatinib, yet exhibit robust sensitivity to covalent TKIs including neratinib, afatinib, and osimertinib, while mutations within exon 19 demonstrate varying sensitivity to lapatinib and covalent inhibitors. Furthermore, studies have demonstrated that HER2 exon 20 mutations have extensive resistance to non-covalent and covalent TKIs such as osimertinib, nazartinib, rociletinib, and olmutinib. Moreover, covalent quinazolinamine-based TKIs neratinib, afatinib, and dacomitinib induce differential responses to individual HER2 exon 20 mutations. However, only uncommon HER2 mutations demonstrated sensitivity to these TKIs at clinically relevant concentrations. More recently, it was reported that poziotinib effectively inhibited HER2 exon 20 insertion mutations at concentrations achievable in patients, and poziotinib treatment induced a radiological response in one patient harboring a HER2 exon 20 mutation. Nevertheless, a single HER2 TKI has not been identified to target the most common variants of HER2 mutant cancers.

SUMMARY

Embodiments of the present disclosure provides methods and compositions for treating cancer in patients with HER2 exon 21 mutations. In one embodiment, there is provided a method of treating cancer in a subject comprising administering an effective amount of poziotinib to the subject, wherein the subject has been determined to have one or more HER exon 21 mutations. In particular aspects, the subject is human.

In some aspects, the poziotinib is further defined as poziotinib hydrochloride salt. In certain aspects, the poziotinib hydrochloride salt is formulated as a tablet.

In certain aspects, the one or more HER2 exon 21 mutations comprise one or more point mutations, insertions, and/or deletions of 1-18 nucleotides between amino acids 832-883. In some aspects, the subject has been determined to have 2, 3, or 4 HER2 exon 21 mutations. In some aspects, the one or more HER2 exon 21 mutations are at one or more residues selected from the group consisting of V842, R868, and L869. In some aspects, the one or more exon 21 mutations are selected from the group consisting of V842I, R868W, and L869R. In some aspects, the one or more HER2 exon 21 mutations are at one or more residues selected from the group consisting of V842 and R868. In some aspects, the one or more exon 21 mutations are selected from the group consisting of V842I and R868W.

In some aspects, the subject is resistant or has shown resistance to the previously administered tyrosine kinase inhibitor. In certain aspects, the tyrosine kinase inhibitor is lapatinib, afatinib, dacomitinib, osimertinib, ibrutinib, nazartinib, or beratinib.

In certain aspects, the poziotinib is administered orally. In some aspects, the poziotinib is administered at a dose of 5-25 mg, such as 6, 7, 8, 9, 10, 11, 12, 13, 14, 15, 16, 17, 18, 19, 20, 21, 2, 23, 24, or 25 mg. In certain aspects, the poziotinib is administered at a dose of 8 mg, 12 mg, or 16 mg. In some aspects, the poziotinib is administered daily. In certain aspects, the poziotinib is administered on a continuous basis. In some aspects, the poziotinib is administered on 28 day cycles.

In certain aspects, the subject was determined to have an HER2 exon 21 mutation by analyzing a genomic sample from the subject. In some aspects, the genomic sample is isolated from saliva, blood, urine, normal tissue, or tumor tissue. In particular aspects, the presence of an HER2 exon 21 mutation is determined by nucleic acid sequencing (e.g., DNA sequencing of tumor tissue or circulating free DNA from plasma) or PCR analyses.

In certain aspects, the method further comprises administering an additional anti-cancer therapy. In some aspects, the anti-cancer therapy is chemotherapy, radiotherapy, gene therapy, surgery, hormonal therapy, anti-angiogenic therapy or immunotherapy. In certain aspects, the poziotinib and/or anti-cancer therapy are administered intravenously, subcutaneously, intraosseously, orally, transdermally, in sustained release, in controlled release, in delayed release, as a suppository, or sublingually. In some aspects, administering the poziotinib and/or anti-cancer therapy comprises local, regional or systemic administration. In particular aspects, the poziotinib and/or anti-cancer therapy are administered two or more times, such as daily, every other day, or weekly.

In some aspects, the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In particular aspects, the cancer is non-small cell lung cancer.

In another embodiment, there is provided a pharmaceutical composition comprising poziotinib for a patient determined to have one or more HER2 exon 21 mutations. In certain aspects, the one or more HER2 exon 21 mutations comprise a point mutation, insertion, and/or deletion of 1-18 nucleotides between amino acids 832-883. In certain aspects, the subject has been determined to have 2, 3, or 4 HER2 exon 21 mutations.

In some aspects, the poziotinib is further defined as poziotinib hydrochloride salt. In certain aspects, the poziotinib hydrochloride salt is formulated as a tablet.

In some aspects, the poziotinib is administered orally. In some aspects, the poziotinib is administered at a dose of 5-25 mg, such as 6, 7, 8, 9, 10, 11, 12, 13, 14, 15, 16, 17, 18, 19, 20, 21, 2, 23, 24, or 25 mg. In some aspects, the poziotinib is administered at a dose of 8 mg, 12 mg, or 16 mg. In certain aspects, the poziotinib is administered daily. In some aspects, the poziotinib is administered on a continuous basis. In some aspects, the poziotinib is administered on 28 day cycles.

In some aspects, the subject is resistant or has shown resistance to the previously administered tyrosine kinase inhibitor. In certain aspects, the tyrosine kinase inhibitor is lapatinib, afatinib, dacomitinib, osimertinib, ibrutinib, nazartinib, or beratinib.

In some aspects, the one or more HER2 exon 21 mutations are at one or more residues selected from the group consisting of V842, R868, and L869. In some aspects, the one or more exon 21 mutations are selected from the group consisting of V842I, R868W, and L869R. In some aspects, the one or more HER2 exon 21 mutations are at one or more residues selected from the group consisting of V842 and R868. In some aspects, the one or more exon 21 mutations are selected from the group consisting of V842I and R868W. In some aspects, the patient is being treated with an anti-cancer therapy.

In yet another embodiment, there is provided a method of predicting a response to poziotinib alone or in combination with an anti-cancer therapy in a subject having a cancer comprising detecting an HER2 exon 21 mutation in a genomic sample obtained from said patient, wherein if the sample is positive for the presence of the HER2 exon 21 mutation, then the patient is predicted to have a favorable response to poziotinib alone or in combination with an anti-cancer therapy. In some aspects, the genomic sample is isolated from saliva, blood, urine, normal tissue, or tumor tissue. In certain aspects, the presence of an HER2 exon 21 mutation is determined by nucleic acid sequencing or PCR analyses. In certain aspects, the HER2 exons 21 mutations comprise one or more point mutations, insertions, and/or deletions of 1-18 nucleotides between amino acids 832-883. In some aspects, the one or more HER2 exon 21 mutations are at one or more residues selected from the group consisting of V842, R868, and L869. In some aspects, the one or more exon 21 mutations are selected from the group consisting of V842I, R868W, and L869R. In some aspects, the one or more HER2 exon 21 mutations are at one or more residues selected from the group consisting of V842 and R868. In some aspects, the one or more exon 21 mutations are selected from the group consisting of V842I and R868W.

In certain aspects, a favorable response to poziotinib inhibitor alone or in combination with an anti-cancer therapy comprises reduction in tumor size or burden, blocking of tumor growth, reduction in tumor-associated pain, reduction in cancer associated pathology, reduction in cancer associated symptoms, cancer non-progression, increased disease-free interval, increased time to progression, induction of remission, reduction of metastasis, or increased patient survival. In further aspects, the patient predicted to have a favorable response is administered poziotinib alone or in combination with a second anti-cancer therapy.

In some aspects, the poziotinib is further defined as poziotinib hydrochloride salt. In certain aspects, the poziotinib hydrochloride salt is formulated as a tablet.

In some aspects, the poziotinib is administered orally. In some aspects, the poziotinib is administered at a dose of 5-25 mg, such as 6, 7, 8, 9, 10, 11, 12, 13, 14, 15, 16, 17, 18, 19, 20, 21, 2, 23, 24, or 25 mg. In some aspects, the poziotinib is administered at a dose of 8 mg, 12 mg, or 16 mg. In certain aspects, the poziotinib is administered daily.

In some aspects, the poziotinib is administered on a continuous basis. In some aspects, the poziotinib is administered on 28 day cycles.

In some aspects, the subject is resistant or has shown resistance to the previously administered tyrosine kinase inhibitor. In certain aspects, the tyrosine kinase inhibitor is lapatinib, afatinib, dacomitinib, osimertinib, ibrutinib, nazartinib, or beratinib.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1J: HER2 mutations occur in a variety of cancer types with mutational hotspots occurring across the receptor. Bar plot of weighted averages of HER2 mutation (A) and HER2 exon 20 mutation (B) frequency by cancer. Bars are representative of the weighted average ±SEM. Dot sizes are representative of number of patients in each database. Frequency of HER2 mutations detected by cfDNA reported by Guardant Health were normalized for clinical sensitivity as reported in Odegaard et al 2018.

FIGS. 4A-4F: Poziotinib was the most potent inhibitor tested for HER2 mutations in Ba/F3 cells. (A) Heatmap of log $IC_{50}$ values calculated in GraphPad for Ba/F3 cells stably expressing the indicated mutations and drugs after 72 hours of drug treatment. Cell viability was determined by the Cell Titer Glo assay (N≥3). Average $IC_{50}$ values for all Ba/F3 cell lines expressing HER2 mutations (B), HER2 exon 19 mutant cell lines (C), HER2 exon 20 mutant cell lines (D), or HER2 exon 21 mutant cell lines (E) after drug treatment for 72 hours with afatinib, neratinib, tarloxotinib-TKI, or poziotinib. Bars are representative of mean±SEM (N≥3). (C-E) One way ANOVA with Dunn's multiple comparisons test was used to determine statistical significance between groups. (F) Average $IC_{50}$ values of Ba/F3 cells expressing L755S or L755P with indicated inhibitors. Dots are representative of mean±SEM (N≥3). Statistical significance was determined by a paired t-test.

FIGS. 7A-7D: NSCLC patients with HER2 mutations have a 42% confirmed response rate to poziotinib. (A) Waterfall plot of first 12 HER2 exon 20 patient responses on clinical trial NCT03066206. Objective partial responses are shown (from left: bar 7, 8, 10, 11, and 12), an unconfirmed response is shown (bar 9), stable disease is shown (bars 3-6), and progressive disease is shown (bars 1-2). (B) Kaplan-meier plot of progression free survival of the first 12 HER2 exon 20 patients demonstrates the mPFS was 5.6 months as of December 2018. (C) CT scan of a patient with a HER2 Y772dupYVMA mutation 1 day before poziotinib treatment and 8 weeks after therapy. (D) PET scans of patient with HER2 L755P mutant NSCLC 1 day before and 4 weeks after poziotinib treatment. Patient had been previously treated and progressed through, platinum based chemotherapy in combination with trastuzumab, nivolumab, and anti TDM1, but had a −12% reduction in target lesions with poziotinib treatment.

FIG. 12: Poziotinib inhibits p-HER2 in HER2 mutant cell lines. Western blot of MCF10A cells expressing G776delinsVC after 2 hours treatment of the indicated drugs and doses.

FIG. 13: Poziotinib inhibits tumor growth in a xenograft of exon 19 mutant colorectal cancer. CW-2 cells harboring a HER2 L755S mutation were injected into the flanks of 6 week old female nu/nu nude mice. When tumors reached 350 mm$^3$ mice were randomized into 4 groups: 20 mg/kg afatinib, 5 mg/kg poziotinib, 30 mg/kg neratinib, or vehicle control. Tumor volumes were measured three times per week, and mice received drug Monday-Friday (5 days per week). Symbols are representative of the mean±SEM for each time point. Two-Way ANOVA with Tukey's multiple comparisons test was used to determine statistical significance. Asterisk indicate significance between vehicle and poziotinib or neratinib. P-values for each comparison are listed below beginning at 10 day when significant differences were first detected.

DESCRIPTION OF ILLUSTRATIVE EMBODIMENTS

Figures 1A, 1B:
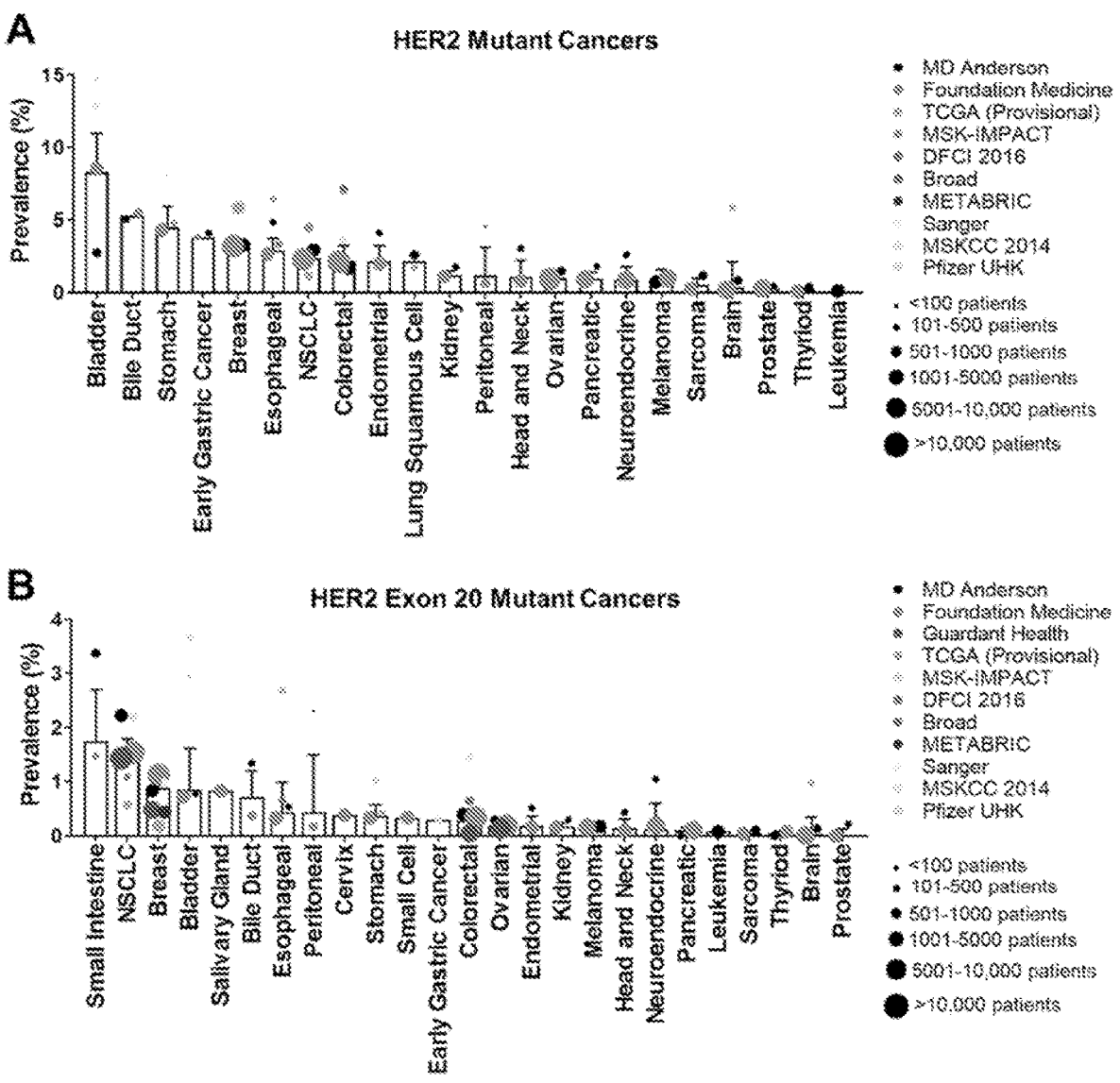

The present studies determined the frequency of the most common genomic variants of HER2 mutations across various malignancies. Systematically, the activating potential of the 16 most frequent HER2 mutations was demonstrated and their drug sensitivity across 11 commonly utilized EGFR and HER2 TKIs was evaluated. It was found that exon 20 insertion mutations and the p.L755P (but not the p.L755S) mutation in exon 19 were refractory to many of the TKIs tested. Molecular dynamic modeling of drug resistant HER2 variants, L755P and exon 20 insertions, demonstrated that these mutations affect the conformational states of the receptor, reducing the overall size of the drug binding pocket. Furthermore, poziotinib was identified as a potent inhibitor of all HER2 mutations evaluated. Moreover, the present studies show that poziotinib has clinical activity in NSCLC patients harboring the most resistant HER2 variants, exon 20 insertions, exon 21 mutations, and L755P. Lastly, the studies show that poziotinib-mediated cell surface receptor accumulation enhances T-DM1 activity that can be exploited to increase anti-tumor activity in vivo, leading to complete tumor regression in a PDX model of HER2 mutant NSCLC.

Accordingly, certain embodiments of the present disclosure provide methods for treating cancer patients with HER2 exon 21 mutations. In particular, the present methods comprise the administration of poziotinib (also known as HM781-36B) or afatinib to patients identified to have HER exon 21 mutations. The size and flexibility of poziotinib overcomes steric hindrance, inhibiting HER2 exon 21 mutants at low nanomolar concentrations. Thus, poziotinib or afatinib as well as structurally similar inhibitors are potent HER2 inhibitors that can be used to target HER2 exon 21 insertions which are resistant to irreversible $2^{nd}$ and $3^{rd}$ generations TKIs.

I. DEFINITIONS

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "about" refers to the stated value plus or minus 5%.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

For example, a treatment may include administration of an effective amount of poziotinib or afatinib.

"Prophylactically treating" includes: (1) reducing or mitigating the risk of developing the disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "insertion(s)" or "insertion mutation(s)" refers to the addition of one or more nucleotide base pairs into a DNA sequence. For example, HER2 exon 21 insertion mutation comprises one or more insertions of 1-18 nucleotides between amino acids 832-883.

"Hybridize" or "hybridization" refers to the binding between nucleic acids. The conditions for hybridization can be varied according to the sequence homology of the nucleic acids to be bound. Thus, if the sequence homology between the subject nucleic acids is high, stringent conditions are used. If the sequence homology is low, mild conditions are used. When the hybridization conditions are stringent, the hybridization specificity increases, and this increase of the hybridization specificity leads to a decrease in the yield of non-specific hybridization products. However, under mild hybridization conditions, the hybridization specificity decreases, and this decrease in the hybridization specificity leads to an increase in the yield of non-specific hybridization products.

A "probe" or "probes" refers to a polynucleotide that is at least eight (8) nucleotides in length and which forms a hybrid structure with a target sequence, due to complementarity of at least one sequence in the probe with a sequence in the target region. The polynucleotide can be composed of DNA and/or RNA. Probes in certain embodiments, are detectably labeled. Probes can vary significantly in size. Generally, probes are, for example, at least 8 to 15 nucleotides in length. Other probes are, for example, at least 20, 30 or 40 nucleotides long. Still other probes are somewhat longer, being at least, for example, 50, 60, 70, 80, or 90 nucleotides long. Probes can be of any specific length that falls within the foregoing ranges as well. Preferably, the probe does not contain a sequence complementary to the sequence(s) used to prime for a target sequence during the polymerase chain reaction.

"Oligonucleotide" or "polynucleotide" refers to a polymer of a single-stranded or double-stranded deoxyribonucleotide or ribonucleotide, which may be unmodified RNA or DNA or modified RNA or DNA.

A "modified ribonucleotide" or deoxyribonucleotide refer to molecules that can be used in place of naturally occurring bases in nucleic acid and includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages.

A "variant" refers to a polynucleotide or polypeptide that differs relative to a wild-type or the most prevalent form in a population of individuals by the exchange, deletion, or insertion of one or more nucleotides or amino acids, respectively. The number of nucleotides or amino acids exchanged, deleted, or inserted can be 1, 2, 3, 4, 5, 6, 7, 8, 9, 10, 11, 12, 13, 14, 15, 16, 17, 18, 19, 20 or more such as 25, 30, 35, 40, 45 or 50.

A "primer" or "primer sequence" refers to an oligonucleotide that hybridizes to a target nucleic acid sequence (for example, a DNA template to be amplified) to prime a nucleic acid synthesis reaction. The primer may be a DNA oligonucleotide, a RNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 10 to about 40 nucleotides long. In certain embodiments, for example, a primer can be 10-40, 15-30, or 10-20 nucleotides long. A primer is capable of acting as a point of initiation of synthesis on a polynucleotide sequence when placed under appropriate conditions.

"Detection," "detectable" and grammatical equivalents thereof refer to ways of determining the presence and/or quantity and/or identity of a target nucleic acid sequence. In some embodiments, detection occurs amplifying the target nucleic acid sequence. In other embodiments, sequencing of the target nucleic acid can be characterized as "detecting" the target nucleic acid. A label attached to the probe can include any of a variety of different labels known in the art that can be detected by, for example, chemical or physical means. Labels that can be attached to probes may include, for example, fluorescent and luminescence materials.

"Amplifying," "amplification," and grammatical equivalents thereof refers to any method by which at least a part of a target nucleic acid sequence is reproduced in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), recombinase-polymerase amplification (RPA) (TwistDx, Cambridg, UK), and self-sustained sequence replication (3 SR), including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, 3rd Edition).

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

II. HER2 EXON 21 MUTATIONS

Certain embodiments of the present disclosure concern determining if a subject has one or more HER2 exon 21 mutations, particularly one or more insertion mutations as depicted in FIG. 2. The subject may have 2, 3, 4, or more HER2 exon 21 mutations. Mutation detection methods are known the art including PCR analyses and nucleic acid sequencing as well as FISH and CGH. In particular aspects, the exon 21 mutations are detected by DNA sequencing, such as from a tumor or circulating free DNA from plasma.

The HER2 exon 21 mutation(s) may comprise one or more point mutations, insertions, and/or deletions of 1-18 nucleotides between amino acids 832-883. In some aspects, the one or more HER2 exon 21 mutations are at one or more residues selected from the group consisting of V842, R868, and L869. In some aspects, the one or more exon 21 mutations are selected from the group consisting of V842I, R868W, and L869R. In some aspects, the one or more HER2 exon 21 mutations are at one or more residues selected from the group consisting of V842 and R868. In some aspects, the one or more exon 21 mutations are selected from the group consisting of V842I and R868W.

In some aspects, the subject may have or develop a mutation at EGFR residue C797 which may result in resistance to the TKI, such as poziotinib. Thus, in certain aspects, the subject is determined to not have a mutation at EGFR C797 and/or T790, such as C797S and/or T790M. In some aspects, subjects with T790 mutations, such as T790M, may be administered osimertinib and subjects with C797 mutations, such as C797S, may be administered chemotherapy and/or radiotherapy.

The patient sample can be any bodily tissue or fluid that includes nucleic acids from the lung cancer in the subject. In certain embodiments, the sample will be a blood sample comprising circulating tumor cells or cell free DNA. In other embodiments, the sample can be a tissue, such as a lung tissue. The lung tissue can be from a tumor tissue and may be fresh frozen or formalin-fixed, paraffin-embedded (FFPE). In certain embodiments, a lung tumor FFPE sample is obtained.

Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine, tumor, or expectorant. The sample itself will typically include nucleated cells (e.g., blood or buccal cells) or tissue removed from the subject including normal or tumor tissue. Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al. (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include urine, blood, and tissue.

The presence or absence of HER2 exon 21 mutations, as described herein can be determined using methods known in the art. For example, gel electrophoresis, capillary electrophoresis, size exclusion chromatography, sequencing, and/or arrays can be used to detect the presence or absence of insertion mutations. Amplification of nucleic acids, where desirable, can be accomplished using methods known in the art, e.g., PCR. In one example, a sample (e.g., a sample comprising genomic DNA), is obtained from a subject. The DNA in the sample is then examined to determine the identity of an insertion mutation as described herein. An insertion mutation can be detected by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular variant.

A set of probes typically refers to a set of primers, usually primer pairs, and/or detectably-labeled probes that are used to detect the target genetic variations (e.g., HER2 exon 21 mutations) used in the actionable treatment recommendations of the present disclosure. The primer pairs are used in an amplification reaction to define an amplicon that spans a region for a target genetic variation for each of the aforementioned genes. The set of amplicons are detected by a set of matched probes. In an exemplary embodiment, the present methods may use TaqMan™ (Roche Molecular Systems, Pleasanton, Calif.) assays that are used to detect a set of target genetic variations, such as HER2 exon 21 mutations. In one embodiment, the set of probes are a set of primers used to generate amplicons that are detected by a nucleic acid sequencing reaction, such as a next generation sequencing reaction. In these embodiments, for example, AmpliSEQ™ (Life Technologies/Ion Torrent, Carlsbad, Calif.) or TruSEQ™ (Illumina, San Diego, Calif.) technology can be employed.

Analysis of nucleic acid markers can be performed using techniques known in the art including, without limitation, sequence analysis, and electrophoretic analysis. Non-limiting examples of sequence analysis include Maxam-Gilbert sequencing, Sanger sequencing, capillary array DNA sequencing, thermal cycle sequencing (Sears et al., 1992), solid-phase sequencing (Zimmerman et al., 1992), sequencing with mass spectrometry such as matrix-assisted laser desorption/ionization time-of-flight mass spectrometry (MALDI-TOF/MS; Fu et al., 1998), and sequencing by hybridization (Chee et al., 1996; Drmanac et al., 1993; Drmanac et al., 1998). Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

Other methods of nucleic acid analysis can include direct manual sequencing (Church and Gilbert, 1988; Sanger et al., 1977; U.S. Pat. No. 5,288,644); automated fluorescent sequencing; single-stranded conformation polymorphism assays (SSCP) (Schafer et al., 1995); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., 1989); denaturing high performance liquid chromatography (DHPLC, Underhill et al., 1997); infrared matrix-assisted laser desorption/ionization (IR-MALDI) mass spectrometry (WO 99/57318); mobility shift analysis (Orita et al., 1989); restriction enzyme analysis (Flavell et al., 1978; Geever et al., 1981); quantitative real-time PCR (Raca et al., 2004); heteroduplex analysis; chemical mismatch cleavage (CMC) (Cotton et al., 1985); RNase protection assays (Myers et al., 1985); use of polypeptides that recognize nucleotide mismatches, e.g., E. coli mutS protein; allele-specific PCR, and combinations of such methods. See, e.g., U.S. Patent Publication No. 2004/0014095, which is incorporated herein by reference in its entirety.

In one example, a method of identifying a HER2 mutation in a sample comprises contacting a nucleic acid from said sample with a nucleic acid probe that is capable of specifically hybridizing to nucleic acid encoding a mutated HER2 protein, or fragment thereof incorporating a mutation, and detecting said hybridization. In a particular embodiment, said probe is detectably labeled such as with a radioisotope ($^3$H, $^{32}$P, or $^{33}$P), a fluorescent agent (rhodamine, or fluorescein) or a chromogenic agent. In a particular embodiment, the probe is an antisense oligomer, for example PNA, morpholino-phosphoramidates, LNA or 2'-alkoxyalkoxy. The probe may be from about 8 nucleotides to about 100 nucleotides, or about 10 to about 75, or about 15 to about 50, or about 20 to about 30. In another aspect, said probes of the present disclosure are provided in a kit for identifying HER2 mutations in a sample, said kit comprising an oligonucleotide that specifically hybridizes to or adjacent to a site of mutation in the HER2 gene. The kit may further comprise instructions for treating patients having tumors that contain HER2 insertion mutations with poziotinib or afatinib based on the result of a hybridization test using the kit.

In another aspect, a method for detecting an exon 21 mutation in a sample comprises amplifying from said sample nucleic acids corresponding to exon 21 of said HER2 gene, or a fragment thereof suspected of containing a mutation, and comparing the electrophoretic mobility of the amplified nucleic acid to the electrophoretic mobility of corresponding wild-type HER2 gene or fragment thereof. A difference in the mobility indicates the presence of a mutation in the amplified nucleic acid sequence. Electrophoretic mobility may be determined on polyacrylamide gel.

Alternatively, nucleic acids may be analyzed for detection of mutations using Enzymatic Mutation Detection (EMD) (Del Tito et al., 1998). EMD uses the bacteriophage resolvase T4 endonuclease VII, which scans along double-stranded DNA until it detects and cleaves structural distortions caused by base pair mismatches resulting from point mutations, insertions and deletions. Detection of two short fragments formed by resolvase cleavage, for example by gel electrophoresis, indicates the presence of a mutation. Benefits of the EMD method are a single protocol to identify point mutations, deletions, and insertions assayed directly from PCR reactions eliminating the need for sample purification, shortening the hybridization time, and increasing the signal-to-noise ratio. Mixed samples containing up to a 20-fold excess of normal DNA and fragments up to 4 kb in size can been assayed. However, EMD scanning does not identify particular base changes that occur in mutation positive samples requiring additional sequencing procedures to identity of the mutation if necessary. CEL I enzyme can be used similarly to resolvase T4 endonuclease VII as demonstrated in U.S. Pat. No. 5,869,245.

III. METHODS OF TREATMENT

Further provided herein are methods for treating or delaying progression of cancer in an individual comprising administering to the individual an effective amount of poziotinib, afatinib, or a structurally similar inhibitor, to a subject determined to have an HER2 exon 21 mutations, such as an exon 21 insertion. The subject may have more than one HER exon 21 mutations.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer. In particular aspects, the cancer is non-small cell lung cancer.

In some embodiments, the subject is a mammal, e.g., a primate, preferably a higher primate, e.g., a human (e.g., a patient having, or at risk of having, a disorder described herein). In one embodiment, the subject is in need of enhancing an immune response. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

Certain embodiments concern the administration of poziotinib (also known as HM781-36B, HM781-36, and 1-[4-[4-(3,4-dichloro-2-fluoroanilino)-7-methoxyquinazolin-6-yl]oxypiperidin-1-yl]prop-2-en-1-one) to a subject determined to have HER2 exon 21 mutations. Poziotinib is a quinazoline-based pan-HER inhibitor that irreversibly blocks signaling through the HER family of tyrosine-kinase receptors including HER1, HER2, and HER4. Poziotinib or structurally similar compounds (e.g., U.S. Pat. No. 8,188, 102 and U.S. Patent Publication No. 20130071452; incorporated herein by reference) may be used in the present methods.

The poziotinib, such as poziotinib hydrochloride salt, may be administered orally, such as in a tablet. The poziotinib may be administered in a dose of 4-25 mg, such as at a dose of 5, 6, 7, 8, 9, 10, 11, 12, 13, 14, 15, 16, 17, 18, 19, 20, 21, 22, 23, or 24 mg. The dosing may be daily, every other day, every 3 days or weekly. The dosing may be on a continuous schedule, such as on 28 days cycles.

In some aspects, subjects with T790 mutations, such as T790M, may be administered osimertinib and subjects with C797 mutations, such as C797S, may be administered chemotherapy and/or radiotherapy as described herein. The osimertinib, chemotherapy, and/or radiation may be administered alone or in combination with poziotinib. Osimertinib may be administered at a dose of 25 to 100 mg, such as about 40 or 80 mg. The dosing may be daily, every other day, every 2 days, every 3 days, or weekly. The osimertinib may be administered orally, such as in tablet.

Afatinib may be administered at a dose of 10-50 mg, such as 10, 20, 30, 40, or 50 mg. The afatinib may be administered daily, every other day, every 2 days, every 3 days, or weekly. The afatinib may be administered orally, such as in tablet.

A. Pharmaceutical Compositions

Also provided herein are pharmaceutical compositions and formulations comprising poziotinib or afatinib and a pharmaceutically acceptable carrier for subjects determined to have a HER2 exon 21 mutation, such as an exon 21 insertion.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

B. Combination Therapies

In certain embodiments, the compositions and methods of the present embodiments involve poziotinib or afatinib in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

The poziotinib or afatinib may be administered before, during, after, or in various combinations relative to an additional cancer therapy, such as immune checkpoint therapy. The administrations may be in intervals ranging from concurrently to minutes to days to weeks. In embodiments where the poziotinib or afatinib is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below poziotinib or afatinib is "A" and an anti-cancer therapy is "B":

A/B/A B/A/B B/B/A A/A/B A/B/B B/A/A A/B/B/B B/A/ B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; Ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., Mycobacterium bovis, Plasmodium falciparum, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824, 311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, Nat Rev Cancer, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos.

US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129; International Patent Publication Nos. WO 01/14424, WO 98/42752, and WO 00/37504 (CP675,206, also known as tremelimumab; formerly ticilimumab); U.S. Pat. No. 6,207,156; Hurwitz et al., 1998; Camacho et al., 2004; and Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application Nos. WO2001014424, and WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. KIT

Also within the scope of the present disclosure are kits for detecting HER2 exon 21 mutations, such as those disclosed herein. An example of such a kit may include a set of exon 21 mutation-specific primers. The kit may further comprise instructions for use of the primers to detect the presence or absence of the specific HER2 exon 21 mutations described herein. The kit may further comprise instructions for diagnostic purposes, indicating that a positive identification of HER2 exon 21 mutations described herein in a sample from a cancer patient indicates sensitivity to the tyrosine kinase inhibitor poziotinib or afatinib or a structurally similar inhibitor. The kit may further comprise instructions that indicate that a positive identification of HER2 exon 21 mutations described herein in a sample from a cancer patient indicates that a patient should be treated with poziotinib, afatinib, or a structurally similar inhibitor.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Identification of Drugs for Cancer Cells with HER2 Exon 21 Mutations HER2 mutations occur most frequently in cancers of the bladder, stomach, and bile duct: To understand the diversity of HER2 mutations across cancer types, several databases were queried including cohorts from cBioPortal, MD Anderson Cancer Center, and Foundation Medicine, and a cfDNA cohort from Guardant Health. Across all databases, all non-synonymous HER2 mutations were analyzed within 25 different cancer types (Table 2). The weighted average frequency for HER2 mutations was calculated. Similar to what was observed in the AACR GENIE database (Meric-Bernstam et al., 2018), HER2 mutations occurred most frequently in bladder (8.3%), bile duct (5.3%), and stomach (4.5%) cancers (FIG. 1A); and HER2 exon 20 mutations occurred most frequently in cancers of the small intestine (1.8%), lung (1.5%), and breast (0.9%) (FIG. 1B).

Figures 2A, 2B, 2C, 2D, 2E:
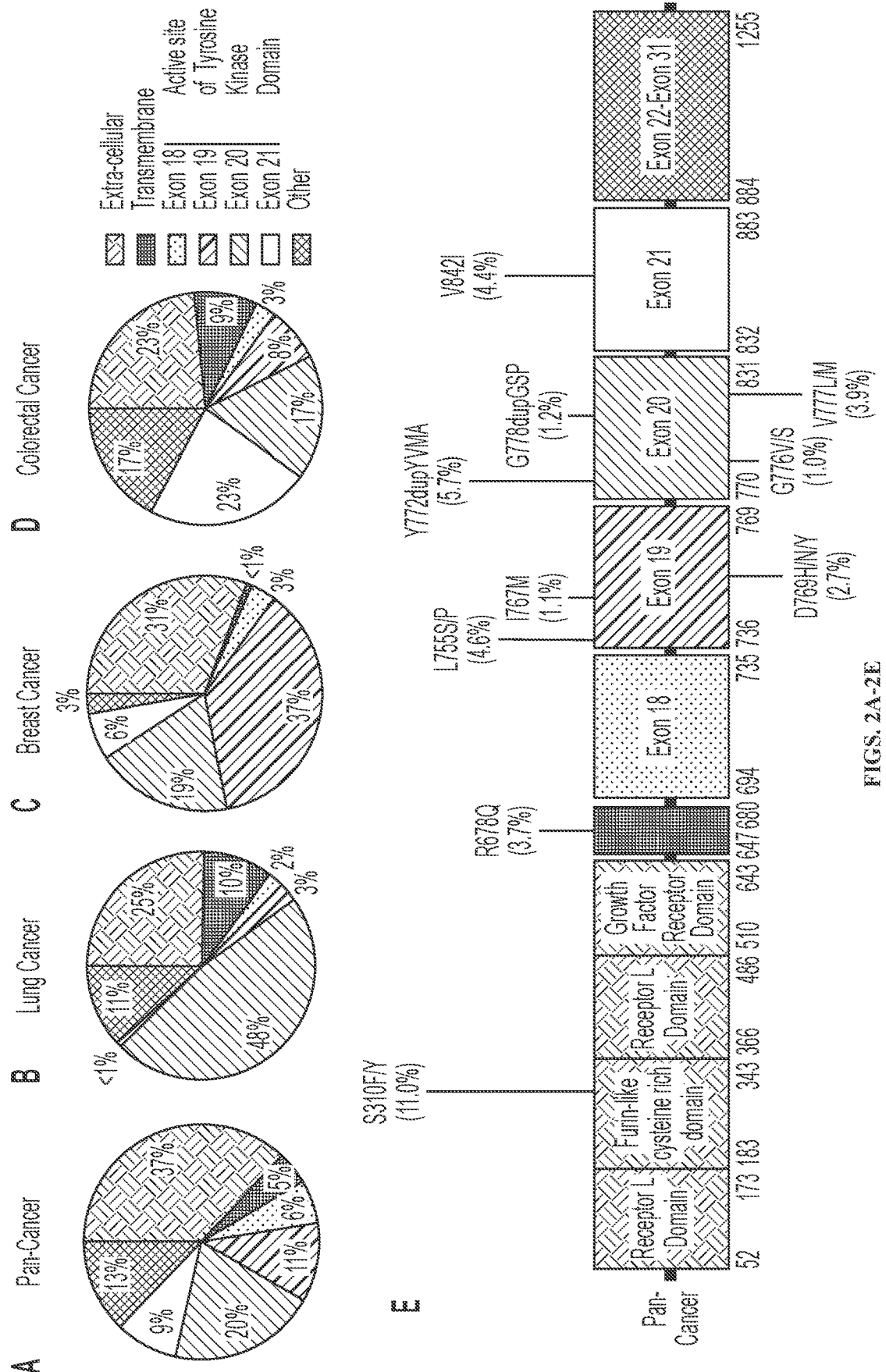
FIGS. 2A-2H: HER2 mutation hotspots vary by cancer type. Pie charts of frequency of HER2 mutation locations across (A) all cancers (N=2338), (B) Lung Cancers (N=177), (C) Breast cancers (N=143), and (D) Colorectal cancers (N=219) reported in cBioportal and MD Anderson databases. (E) Lollipop plot of the 10 most common HER2 mutations across all cancers reported in cBioPortal and MD Anderson (N=2338 HER2 mutations). Length of bars are relative to frequency of mutation. (E-H) Lollipop plots of the 10 most common HER2 mutations across NSCLC (F, N=177), Breast cancer (G, N=143), and Colorectal cancer (H, N=219) in cBioPortal and MD Anderson databases; length of bars are relative to frequency of mutation reported.
Figures 2F, 2G:
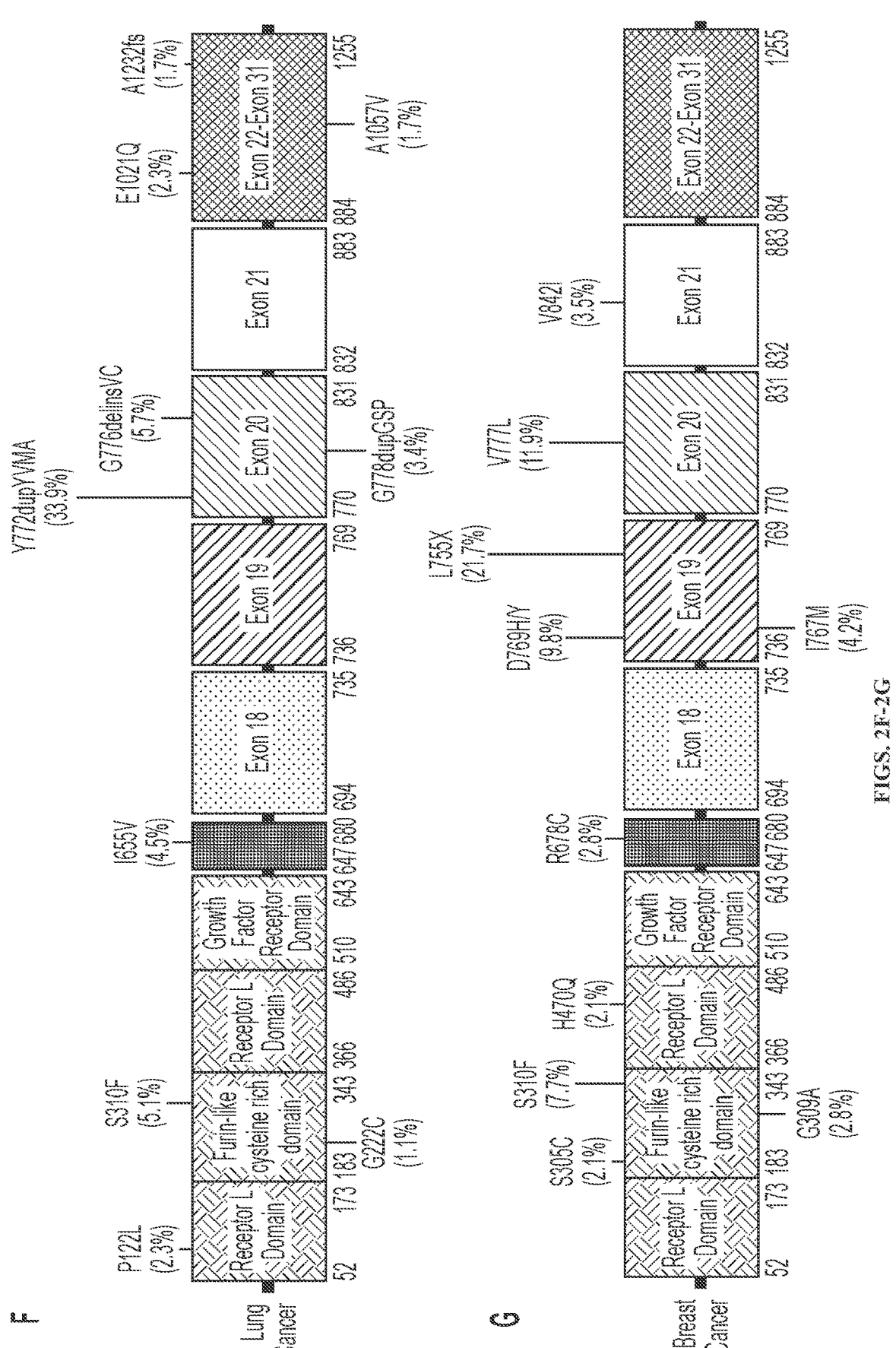
Figure 2H:
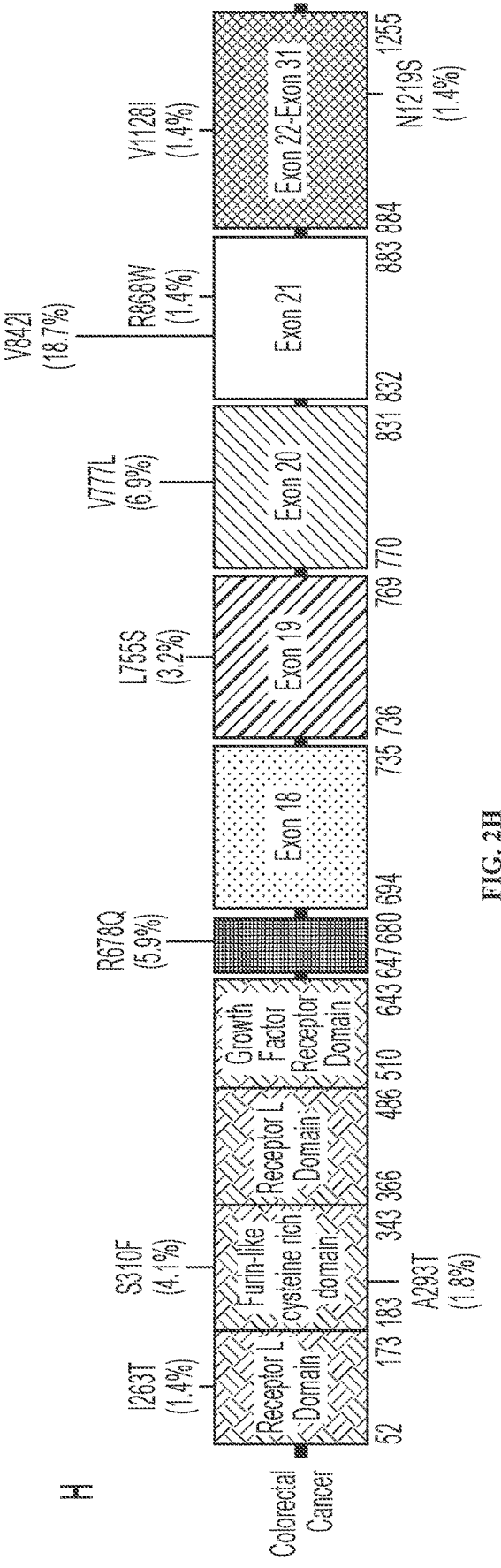

HER2 mutations occur most frequently in the tyrosine kinase domain of HER2 and mutational hotspots vary by malignancy: Next, the frequency of mutations was analyzed within the various regions of the HER2 receptor reported in cBioPortal and at MD Anderson. Across all cancer types, HER2 mutations occurred most frequently in the tyrosine kinase domain (46%) which included mutations in exon 20 (20%), exon 19 (11%), and exon 21 (9%) (FIG. 2A). In addition, extra-cellular domain mutations made up 37% of HER2 mutations. Across all cancers queried, the most common HER2 mutations were p.S310F/Y (11.0%), p.Y772_A775dupYVMA (5.7%), p.L755P/S (4.6%), p.V842I (4.4%), and p.V777L/M (4.0%) (FIG. 2E). In lung cancer, the majority of HER2 mutations occurred within exon 20 (48%), with Y772_A775dupYVMA comprising 34% of all HER2 mutations (FIGS. 2B, 2F). In breast cancer, the majority of HER2 mutations occurred within exon 19 (37%), with L755 mutations being the most prevalent at 22% of HER2 mutations (FIG. 2C). However, unlike lung cancer where one variant was dominant, in breast cancer, there was more mutational diversity among exon 19 mutations (FIG. 2G). In colorectal cancer, HER2 mutations occurred most frequently in exon 21 (23%) and the extra-cellular domain (23%), with the V842I variant in exon 21 being the most prevalent (19%) (FIGS. 2D, 2H).

Figures 9A, 9B, 9C, 9D:
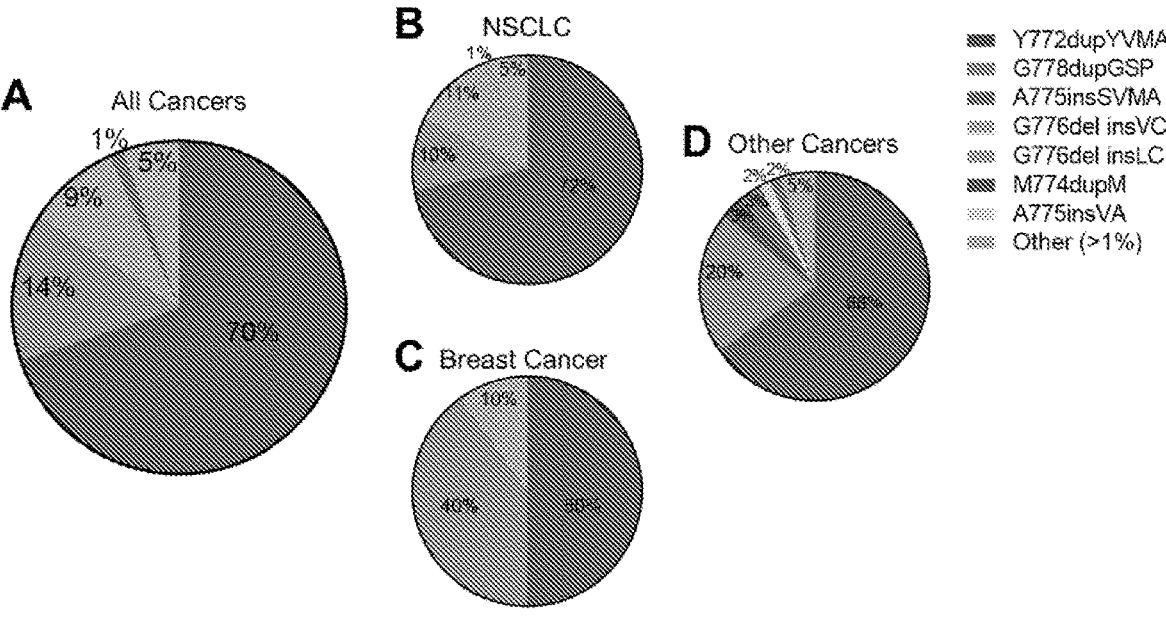
FIGS. 9A-9D: Exon 20 insertion mutation diversity differs by cancer type in Guardant, cBioPortal, and MD Anderson databases. Pie charts of HER2 exon 20 insertion mutation frequency in (A) all cancer types, N=517. Frequency of exon 20 insertion mutations were further analyzed by cancer types: (B) Lung cancer, N=362, (C) Breast cancer, N=30, and (D) other cancers, N=125.

Y772dupYVMA is the most common HER2 exon 20 insertion mutation across cancer types: HER2 exon 20 mutations are the most commonly occurring mutations within the tyrosine kinase domain of HER2 (16% of all HER2 mutations and 43% of tyrosine kinase domain mutations), and HER2 exon 20 insertion mutations remain a clinical challenge. To understand the diversity and prevalence of exon 20 insertions, the frequency of HER2 exon 20 insertion sequences was analyzed by cancer type in cBioportal, MD Anderson, and Guardant Health databases. The Y772dupYVMA insertion was the most common HER2 exon 20 insertion, comprising 70% of all HER2 exon 20 insertions, and the p.G778dupGSP (14%) and p.G776del insVC (9%) insertions occurred the second and third most frequently (FIG. 9A). Exon 20 insertion mutations in NSCLC (N=362) showed the greatest diversity in exon 20 insertion mutations (FIG. 9B), and exon 20 insertion mutations in breast cancer (N=30) showed little diversity in insertion sequence with only three distinct variants reported (FIG. 9C). Additional rare insertion mutations were seen across other cancer types, but the duplications at Y772 and G778 occurred most frequently in every cancer type analyzed (FIG. 9D).

Figures 3A, 3B, 3C:
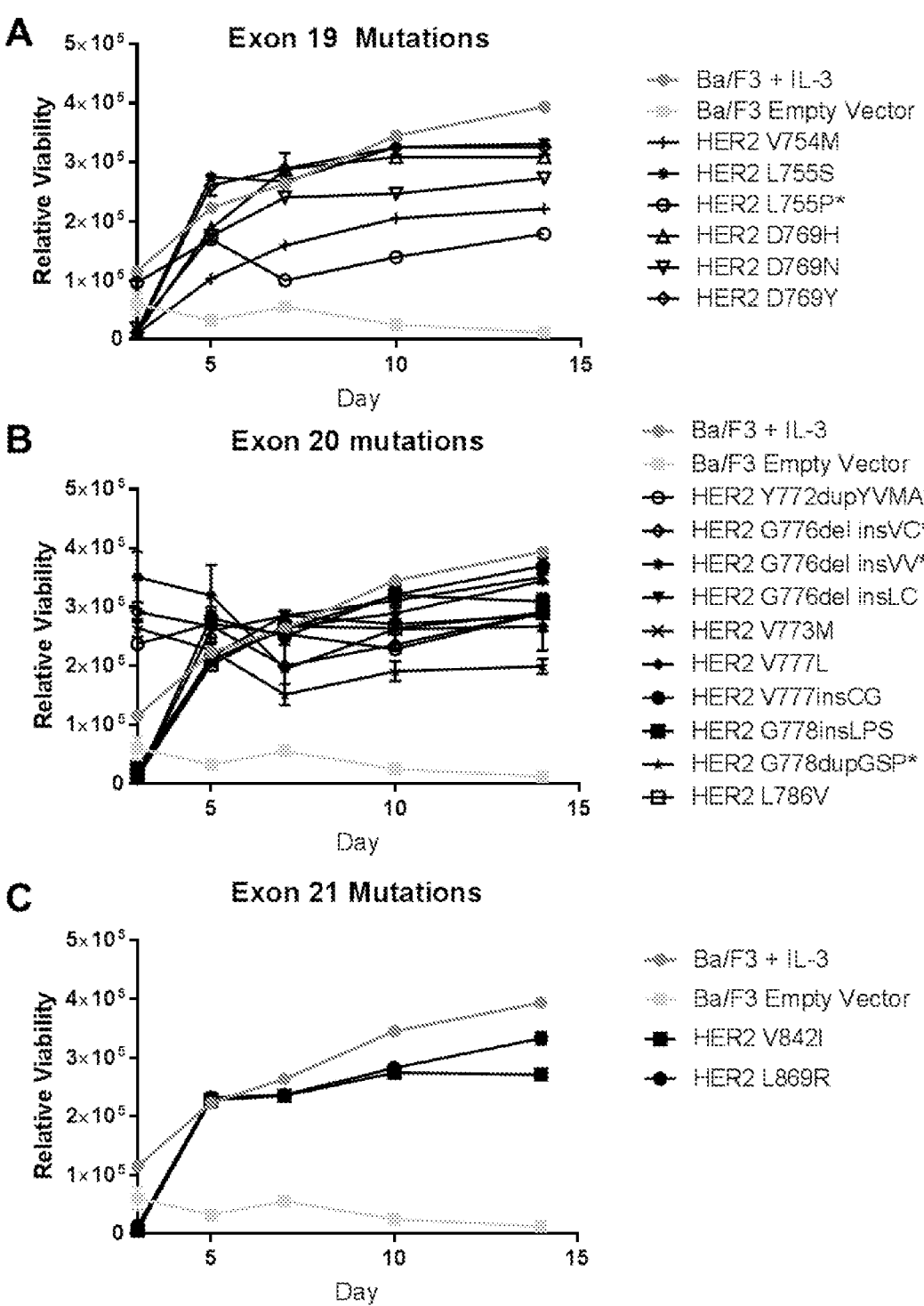
FIGS. 3A-3C: The most common HER2 variants in the tyrosine kinase domain are activating mutations. Cell viability of stable Ba/F3 cell lines expressing HER2 exon 19 (A), HER2 exon 20 (B), and HER2 exon 21 (C) mutations grown in IL-3 free conditions for 14 days. Cell viability was determined every 3 days by the Cell Titer Glo assay. The mean±SEM is plotted for each cell line (n=3 biologically independent experiments).
Figures 10A, 10B:
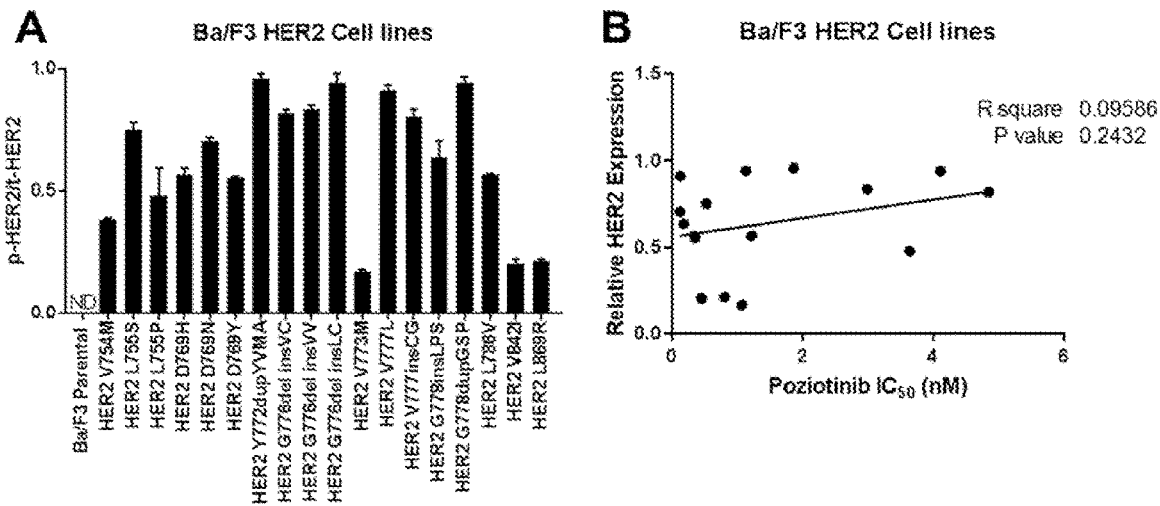
FIGS. 10A-10B: Common HER2 mutations are constitutively phosphorylated and p-HER2 expression does not correlate with drug sensitivity. (A) Relative p-HER2 expression was determined by taking the ratio of p-HER2 over total HER2 as determined by ELISA. Bars are representative of the mean±SEM, and n=3. ND=below the limit of detection. (B) Correlation of the relative HER2 was plotted against poziotinib IC50 values for Ba/F3 HER2 mutant cell lines. Pearson correlations and p-values were determined by GraphPad Prism (n=3).

Frequently detected HER2 alterations are activating mutations: To assess the functional impact of common HER2 mutations, Ba/F3 cells were stably expressed with the 16 most frequently detected HER2 mutation across exons 19, 20, and 21. All 16 HER2 mutations tested were found to induce IL-3 independent survival of Ba/F3 cells (FIGS. 3A-C). Moreover, expression of these 16 HER2 mutations resulted in expression of phosphorylated HER2 (FIG. 10A), indicating that these mutations result in receptor activation.

Figure 4A:
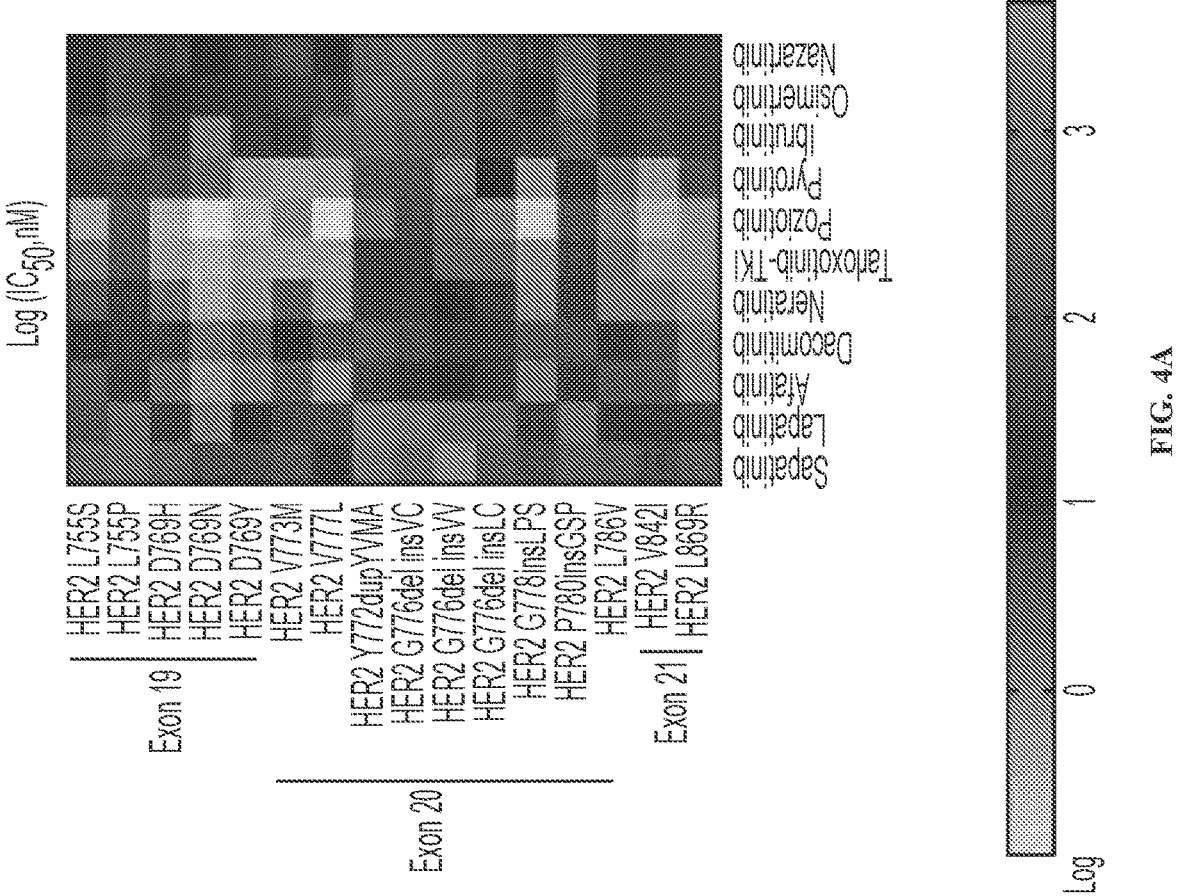

Poziotinib was the most potent TM tested and inhibited the most common HER2 mutations in vitro: While recent reports highlight the effectiveness of covalent quinazolin-amine-based TKIs (i.e. afatinib, dacomitinib, poziotinib, neratinib) in pre-clinical models of HER2 mutant disease, clinical studies of afatinib, dacomitinib, and neratinib have had low ORRs, as well as cancer-specific and variant-specific differences in patient outcomes. To systematically evaluate drug sensitivity across the most commonly detected HER2 variants, the panel of HER2 mutant Ba/F3 cells was screened against 11 covalent and non-covalent EGFR and HER2 TKIs. HER2 mutants showed robust resistance to non-covalent inhibitors, lapatinib and sapatinib (FIG. 4A). Covalent TKIs osimertinib, ibrutinib, and nazartinib were not effective in inhibiting cell viability in cells expressing exon 20 mutations; however, these TKIs did demonstrate activity against cells expressing D769 variants (FIG. 4A). By comparison, covalent, quinazolinamine-based TKIs, afatinib, neratinib, dacomitinib, tarloxotinib-TKI, and poziotinib, had inhibitory activity for HER2 mutants across all three exons (FIG. 4A). Across all HER2 mutation variants and TKIs tested, poziotinib had the lowest average $IC_{50}$ and was significantly more effective in reducing cell viability than afatinib, neratinib, or tarloxotinib-TKI (FIG. 4B). In addition, while poziotinib was significantly more efficacious than either afatinib, neratinib, or tarloxotinib-TKI against HER2 exon 19 and 20 mutations, there was no significant difference in average $IC_{50}$ for exon 21 mutants (FIGS. 4C-E), suggesting that mutation location impacts drug binding. Furthermore, within exon 19, L755S and L755P variants had significant differences in drug sensitivity across all TKIs tested (FIG. 4F), indicating that specific amino acid changes at this site influenced drug binding affinity.

Figures 5A, 5B, 5C, 5D:
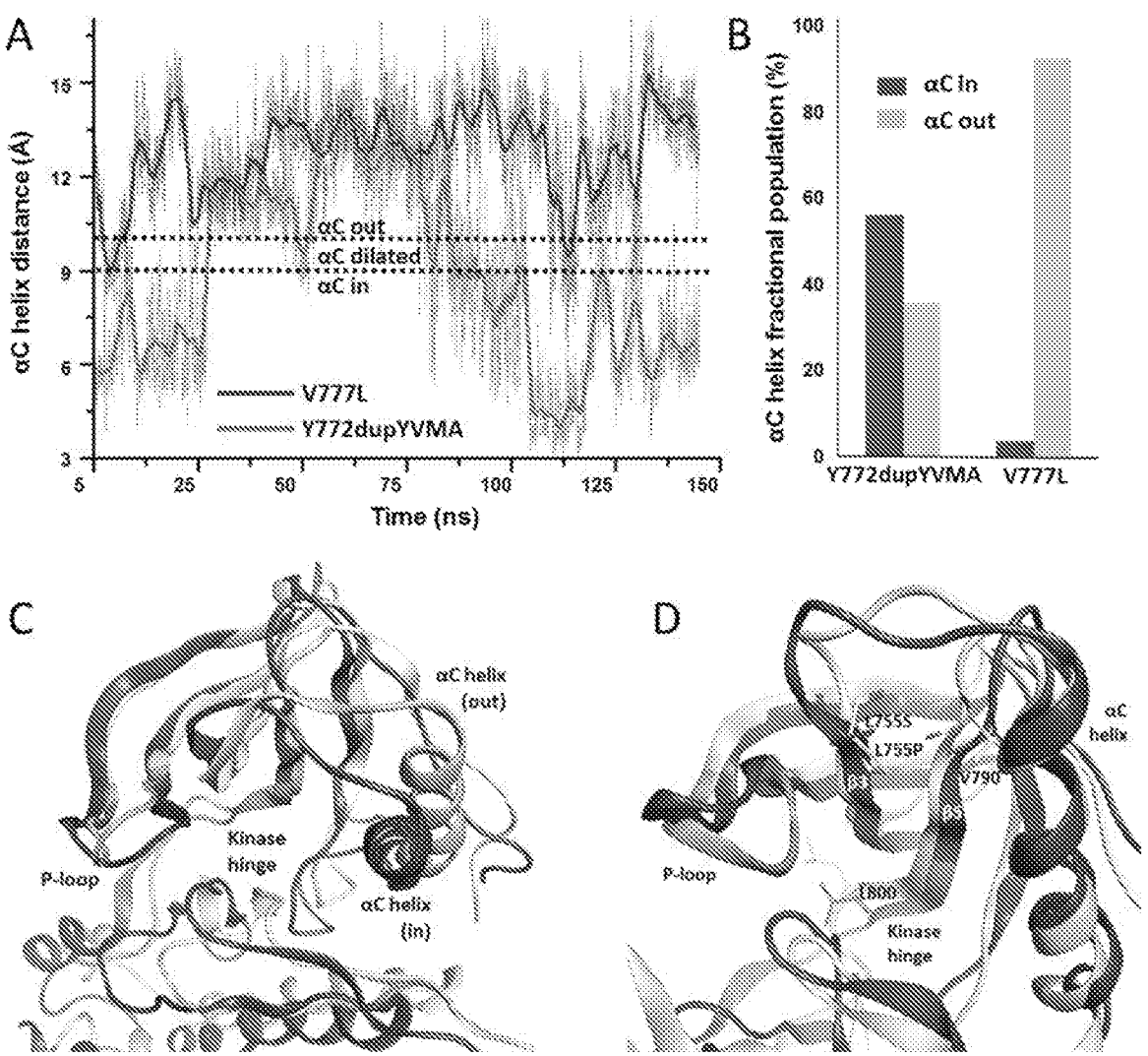
FIGS. 5A-5D: Molecular dynamics simulations of HER2 mutants reveal possible mechanisms for decreased drug sensitivity for Y772dupYVMA and L755P mutations. (A) α-C-helix positions for the HER2 V777L and Y772dupYVMA exon 20 mutants during the 150 ns accelerated molecular dynamics simulations. (B) Fractional population of molecular dynamics snapshots for the HER2 exon 20 mutants in the α-C-helix "in" vs. "out" conformations. (C) Molecular dynamics snapshots of the V777L and Y772dupYVMA mutants. There are minor differences in P-loop and kinase hinge conformations, but a significant shift in α-C-helix position ("out" position for V777L, "in" position for Y772dupYVMA). (D) Molecular dynamics snapshots of L755P and L755S HER2 mutants. The L755P mutant lacks a backbone hydrogen bond with V790, leading to destabilization of the kinase hinge and contraction of the P-loop towards the binding site.
Figure 11A:
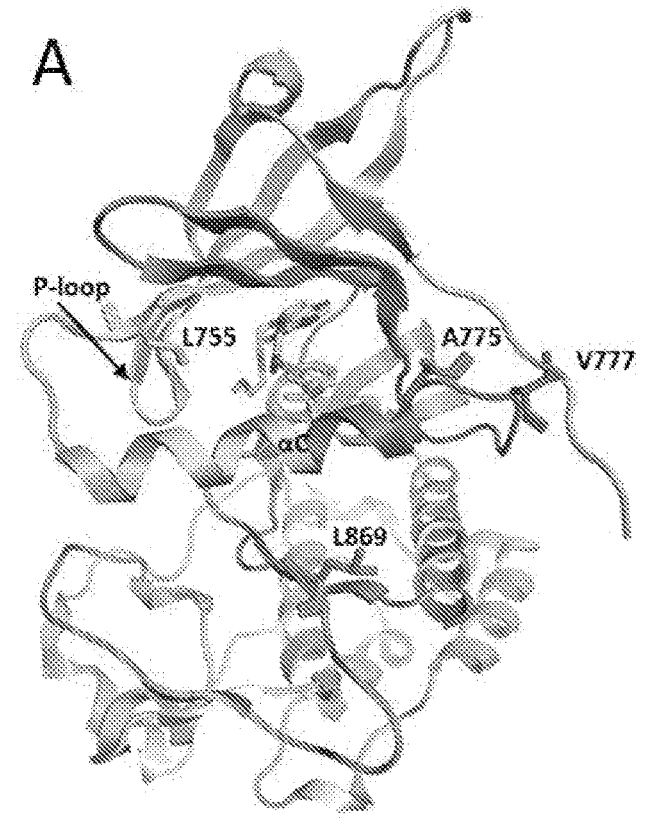
FIGS. 11A-11B: Molecular modeling reveals HER2 mutants differ in binding pocket size. (A) HER2 kinase domain exon 19, 20 and 21 protein backbone colored in blue, pink, and orange, respectively. The ligand from the template X-ray structure (PDB 3PP0) is rendered in green sticks and labels are provided for mutated residues/insertion locations. (B) Binding pocket volume profiles for the HER2 mutants taken from the accelerated molecular dynamics simulations.
Figure 11B:
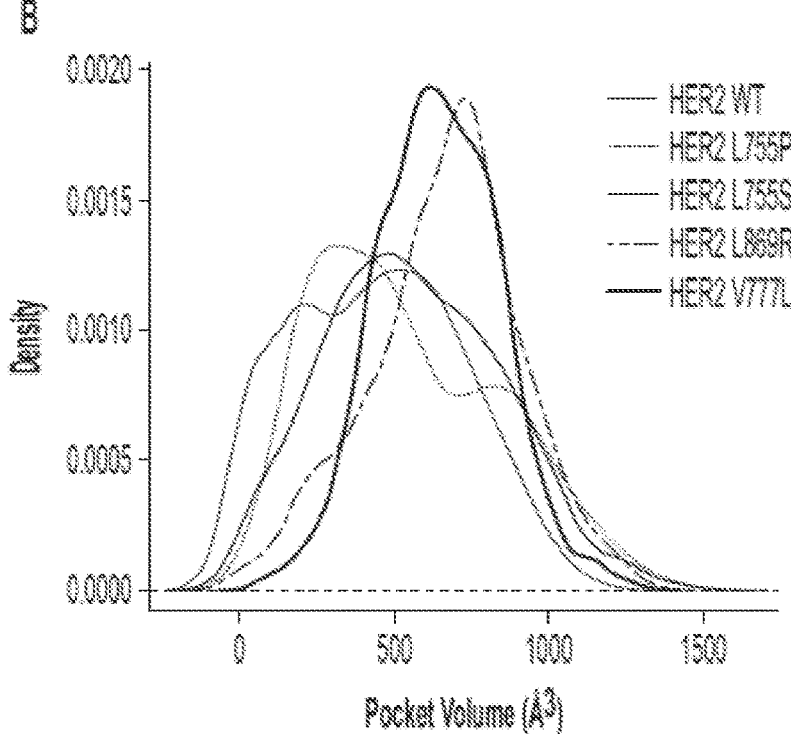

HER2 mutation location and amino acid change affects drug binding affinity: To further understand how the location of the mutation and the amino acid change can affect drug binding affinity and inhibitory efficacy, molecular dynamics simulations were used to investigate how these mutations impact the structure and dynamics of the HER2 kinase domain. Molecular models of the L755S, L755P, Y772dupYVMA, and V777L HER2 mutants (FIG. 11A) were constructed using a publicly available X-ray structure (PDB 3PP0) as a template and subjected to accelerated molecular dynamics to increase protein conformational sampling. The range of protein conformations sampled, particularly in regard to the P-loop and $\alpha$-C-helix positions, varied among these HER2 mutants. Differences were clearly evident even between exon 20 mutations, especially in the $\alpha$-C-helix region, where the duration of the conformation of the $\alpha$-C-helix varied between the "in" (the active conformation with a smaller binding pocket), and the "out" (the inactive conformation with a larger binding pocket). The V777L mutant heavily sampled the "out" conformation while the Y772dupYVMA mutant sampled both the "in" and "out" conformations (FIG. 5A). Overall, these differences in conformational state resulted in the Y772dupYVMA mutant residing in the "in" conformation 10-times more often than the V777L mutant (FIG. 5B), and, on average, a smaller binding pocket size for Y772dupYVMA compared to V777L (FIGS. 5C and 11B). In addition, the smaller binding pocket of the Y772dupYVMA may be the cause of the weaker potency of neratinib against the Y772dupYVMA compared to the V777L since neratinib contains a pyridyl ring oriented towards the $\alpha$-C-helix.

Further analysis of the HER2 mutant binding pocket volumes (FIG. 10B) demonstrated that mutations at the same residue can have drastically different effects on protein conformation. In particular, the proline residue of the L755P mutation lacks a hydrogen bond donor which breaks a backbone hydrogen bond between the $\beta 3$ and $\beta 5$ strands between L755 and V790, respectively. The lack of stabilization between these two $\beta$-strands resulted in destabilization of the $\beta$-sheet and a structural rearrangement in the kinase hinge region (FIG. 5D). In particular the L800 residue of L755P protruded into the active site and reduced the pocket size considerably. Changes in the $\beta 3$ strand conformation also caused the P-loop to collapse inward, further reducing pocket volume and making this mutant less sensitive to most TKIs. Furthermore, the changes in hinge mobility may also play a role in kinase activation. These distinct changes in the L755P mutant confirmation contrasted with the behavior of the L755S mutant, which had a conformational and pocket volume profile that is more similar to wild-type HER2 (FIG. 11B).

HER2 mutant human cancer cell lines showed enhanced sensitivity to poziotinib: Clinical studies testing HER2 inhibitors have revealed cancer type specific differences in drug sensitivity (Hyman et al., 2018). To determine whether covalent, quinazolinamine-based TKIs have activity in models of HER2 mutant disease, the panel of EGFR/HER2 TKIs were tested in human cancer cell lines. Pre-neoplastic MCF10A mammary epithelial cells were transfected with HER2 exon 20 mutations and evaluated in vitro sensitivity to 12 EGFR/HER2 TKIs. MCF10A cells expressing G776del insVC, Y772dupYVMA, or G778dupGSP HER2 mutations were most sensitive to poziotinib, with $IC_{50}$ values of 12 nM, 8.3 nM, and 4.5 nM, respectively (FIG.

Figures 6A, 6B:
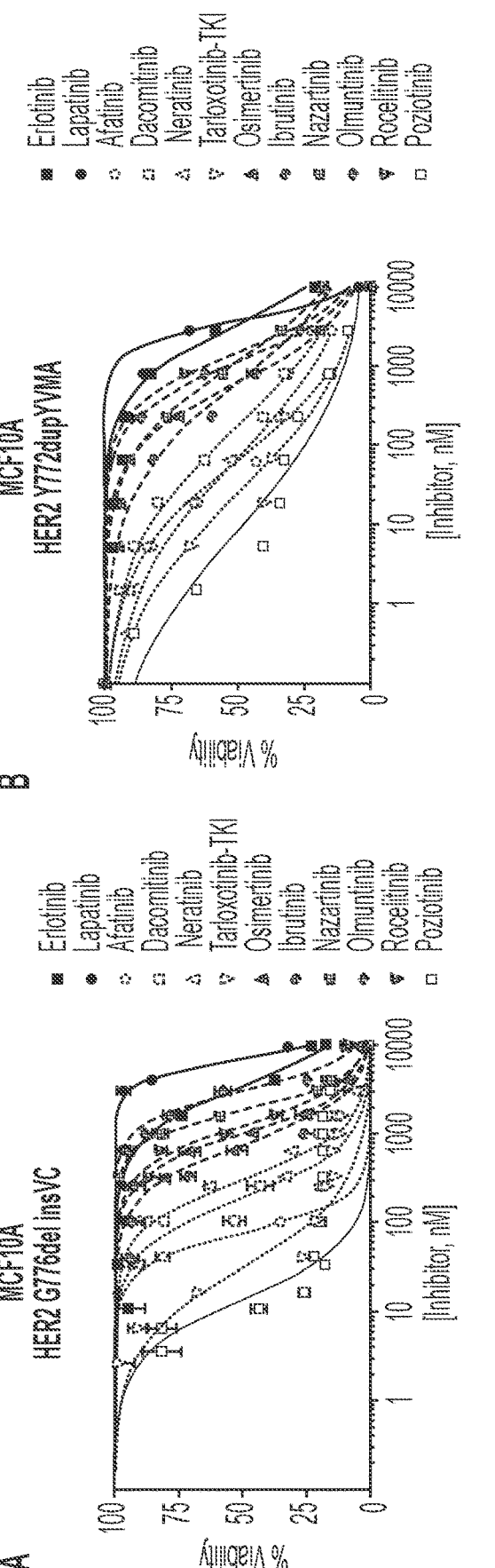
FIGS. 6A-6F: Human cell lines expressing HER2 mutations are also most sensitive to poziotinib. Dose response curves of MCF10A cells expressing exon 20 insertion mutations, HER2 G776delinsVC (A), HER2 Y772dupYVMA (B), HER2 G778dupGSP (C), treated with indicated inhibitors for 72 hours. (D) Bar graph of MCF10A HER2 selectivity index. $IC_{50}$ values of mutant cell lines were divided by average $IC_{50}$ value of HER2 WT expressing cell line for each indicated drug. Dots are representative of mean±SEM for each cell line and bars are representative of mean±min/max of all three cell lines (N≥3 for each cell line). (E) Dose response curve of CW-2 large intestine cells harboring HER2 exon 19 mutation L755S treated with indicated inhibitors for 72 hours. (A-C, E) Curves are representative of mean±SEM, N=3. (F) Bar graph of CW-2 tumor volume at day 21. Mice were treated with vehicle control (N=5), 30 mg/kg neratinib (N=5), 20 mg/kg afatinib (N=5), or 5 mg/kg poziotinib (N=5) 5 days/week and tumors were randomized at 350 mm³, indicated by the dotted line. Dots are representative of individual tumors, and bars are representative of mean±SEM. Statistical significance was determined by one-way ANOVA.
Figures 6C, 6D:
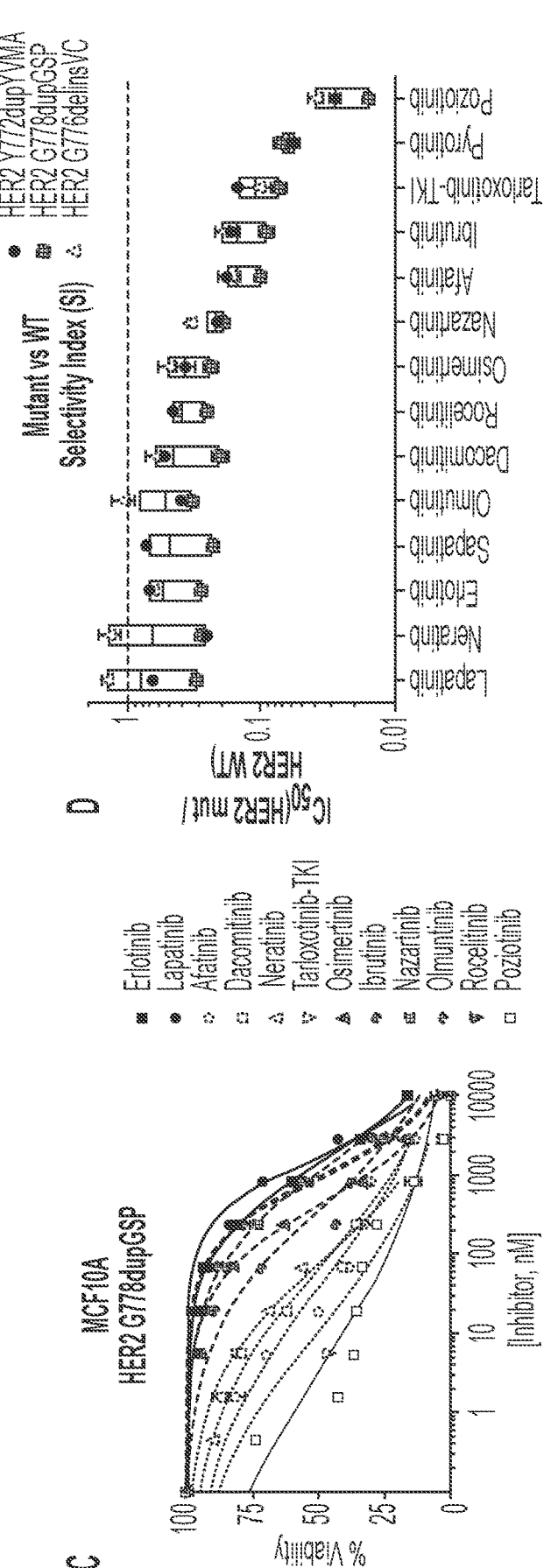
Figure 6E:
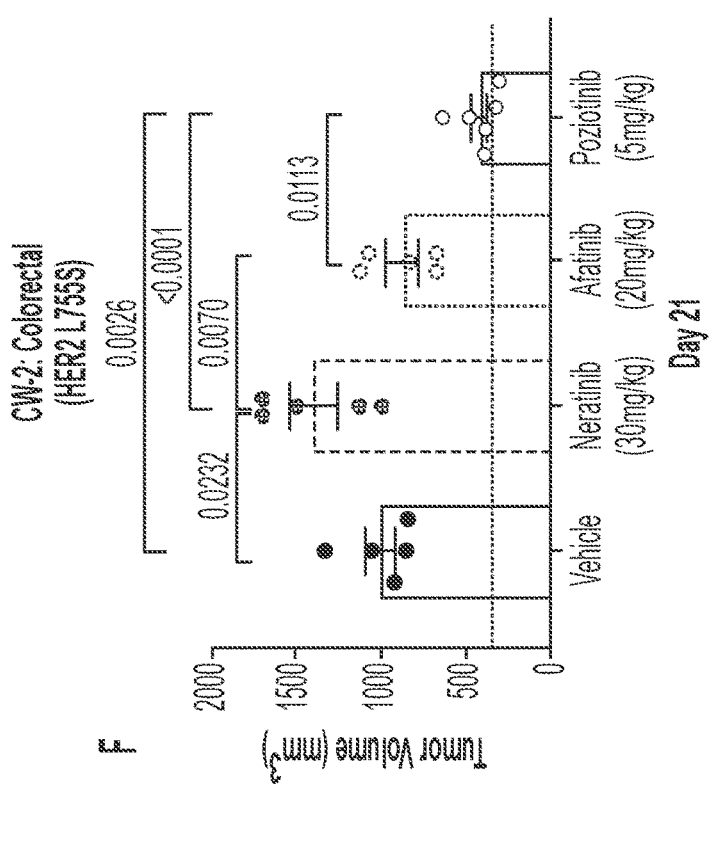
Figure 6F:
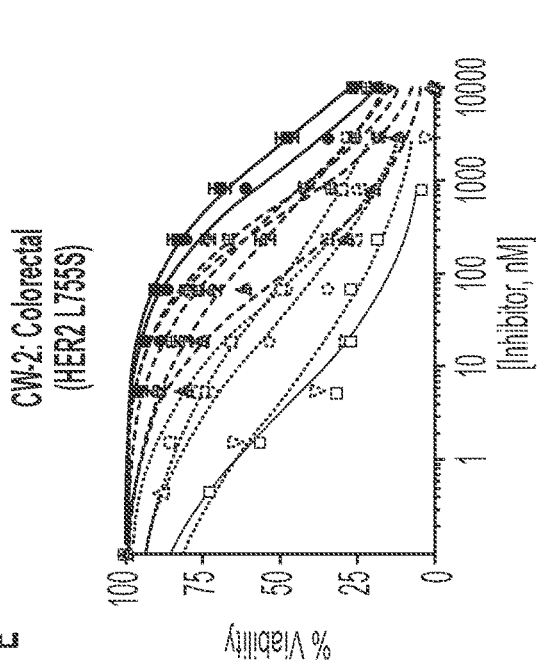

6A-C). In comparison, tarloxotinib-TKI and neratinib yielded average $IC_{50}$ values of 21 nM and 150 nM, respectively (FIGS. 6A-C), indicating that poziotinib is 2.6 and 19 times more potent than tarloxotinib-TKI and neratinib, respectively (p<0.001). Furthermore, Western blotting of MCF10A HER2 G776delinsVC cells with poziotinib and neratinib showed that poziotinib, but not neratinib, completely inhibits p-HER2 at 10 nM (FIG. 12A). Since wild-type (WT) HER2 does not transform Ba/F3 cells to grow independent of IL-3, MCF10A cells were used to determine the selectivity of the TKIs for mutant HER2 compared to WT HER2. To this end, the selectivity index (SI, $IC_{50}$ value mutant/$IC_{50}$ value WT) was calculated for each inhibitor, and found that poziotinib was the most mutant selective TKI tested in MCF10A cell lines (SI=0.028), followed by pyrotinib (SI=0.063) and tarloxotinib-TKI (SI=0.111), (FIG. 6D). Consistent with the data obtained using Ba/F3 cells (FIG. 3C), in a model of HER2 exon 19 mutant colorectal cancer (CW-2), differences in sensitivity between poziotinib, tarloxotinib-TKI, and neratinib were less dramatic, albeit significant (p=0.02 and p=0.0004), with average $IC_{50}$ values of 3.19 nM, 4.24 nM, and 68.8 nM, respectively (FIG. 6E). Furthermore, in a xenograft mouse model of CW-2 colorectal cells, at day 21, poziotinib (5 mg/kg) treated animals had showed a reduction of 58% in tumor volume compared to the vehicle treated group (p=0.011). In comparison, neratinib (30 mg/kg) treated animals showed an increased tumor volume (28%) compared to vehicle control (p=0.023), and afatinib (20 mg/kg) treatment did not significantly affect tumor growth compared to vehicle control (FIGS. 6F, 13).

Figure 7A:
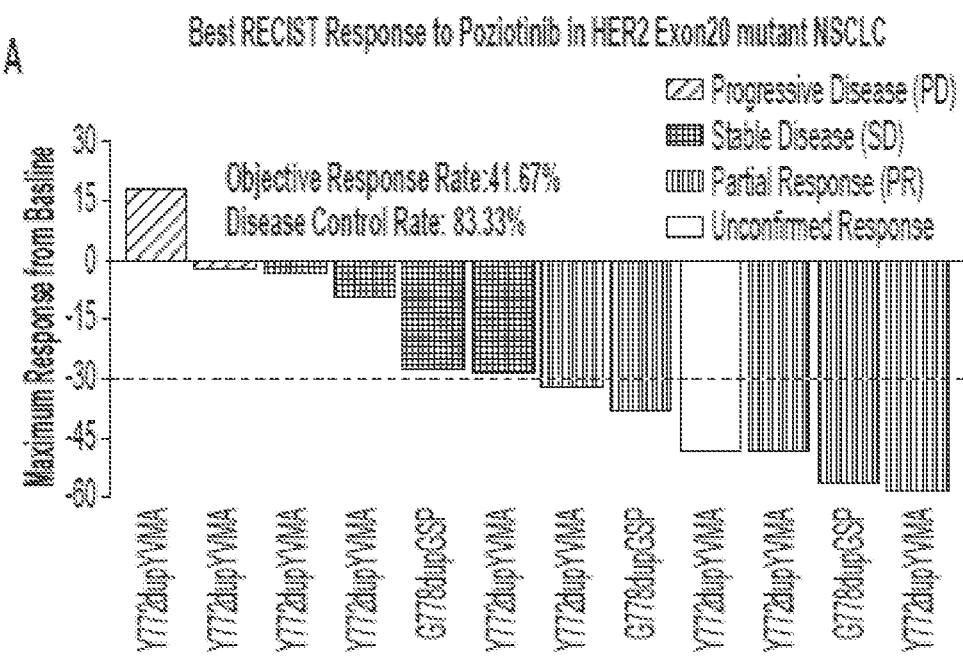
Figure 7B:
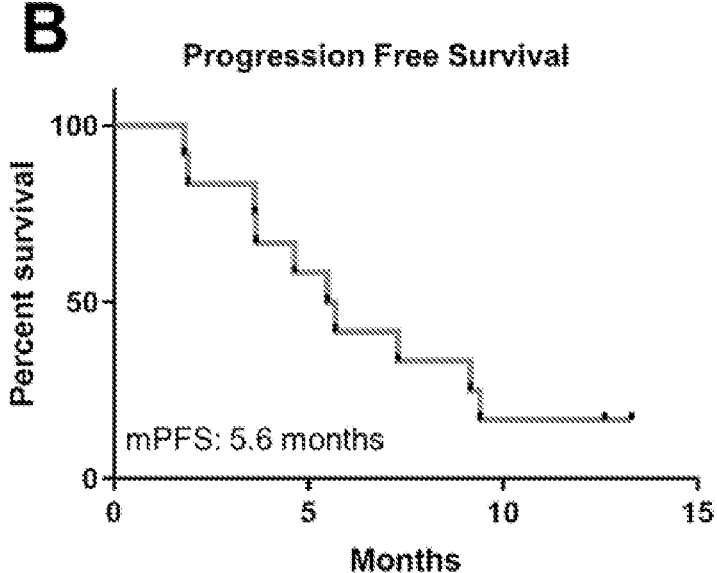

Poziotinib has anti-tumor activity in NSCLC patients with HER2 mutations: Based on these preclinical data and previously published work on exon 20 mutations (Robichaux et al., 2018), an investigator-initiated, phase II clinical trial of poziotinib in EGFR and HER2 exon 20 mutant NSCLC (NCT03066206) was initiated. Patients were treated with poziotinib 16 mg orally daily until progression, death, or withdrawal. Objective response was evaluated every eight weeks, based on RECIST v1.1. Of the first 12 evaluable patients harboring HER2 exon 20 insertion mutations, 6/12 (50%) patients had a best response of partial response (PR). This response was confirmed by a repeat scan 2 months later in 5/12 (confirmed objective response rate, 42%) (FIG. 7A). Of these twelve patients, two patients had progressive disease (PD) at first response evaluation, resulting in a disease control rate (DCR) of 83%. As of December 2018, ten of the twelve patients had progressed, and the median PFS for the first twelve patients was 5.6 months (FIG. 7B). All patients included in the study thus far harbored one of the two most common HER2 exon 20 insertions, Y772dupYVMA and G778dupGSP (FIG. 7A). Representative images of one NSCLC patient with an Y772dupYVMA mutation pre- and post-treatment (8 weeks) showed robust tumor shrinkage in the right lung (FIG. 7C). Patient characteristics including number of previous lines of treatment can be found in Table 3. In addition, one heavily pre-treated NSCLC patient harboring a HER2 exon 19 point mutation, L755P, was treated on a compassionate care use protocol (C-IND18-0014). The patient was treated with 16 mg poziotinib daily and had tumor shrinkage at four weeks (FIG. 7D, white box). The patient had stable disease (SD) per RECIST v1.1 (−12% reduction in target legions). The patient remained on poziotinib with disease control for more than seven months until imaging revealed disease progression and poziotinib was discontinued. The patient was clinically well at the end of poziotinib treatment and proceeded to receive further systemic therapy.

Figure 8A:
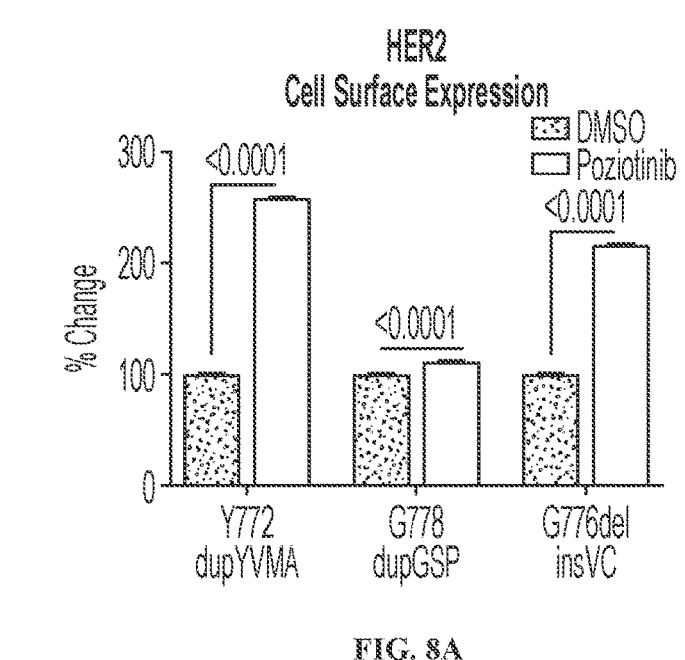
FIGS. 8A-8G: Poziotinib treatment induces accumulation of HER2 on the cell surface, and combination of poziotinib and T-DM1 treatment potentiates anti-tumor activity. (A) FACS analysis of HER2 receptor expression on MC10A cell lines expressing HER2 Y772dupYVMA, HER2 G778dupGSP, and HER2 G776delinsVC after 24 hours of 10 nM poziotinib treatment. Bars are representative of mean±SEM, and significant differences were determined by students' t-test between DMSO and poziotinib treated groups. (B) Bar graphs of $IC_{50}$ values of MCF10A cell lines expressing HER2 Y772dupYVMA, HER2 G778dupGSP, and HER2 G776delinsVC treated with poziotinib, T-DM1 or poziotinib and indicated dose of T-DM1. Bars are representative of mean±SEM (n=3 independent experiments), and significant differences were determined by One-way ANOVA and Dunn's multiple comparison post-hoc. (C) Tumor growth curves of HER2 Y772dupYVMA NSCLC PDX treated with the indicated inhibitors. Poziotinib treatment was administered five days per week, and T-DM1 was administered once at the beginning of treatment. (D) Kaplan-Meier curve of progression free survival (PFS), where PFS is defined as tumor doubling from best response. Mantel-Cox Log rank test was used to determine significant differences between groups. Mice were censored at time of euthanasia. (E) Dot plot of percent change in tumor volume of mice treated with indicated inhibitors at day 15. (F) Chart of number of tumor bearing mice in each group at day 15 and day 45. (G) Spider plots of tumor volume of HER2 Y772dupYVMA mice treated with indicated inhibitors. The dotted line indicates the point of randomization (300 mm$^3$).
Figure 8B:
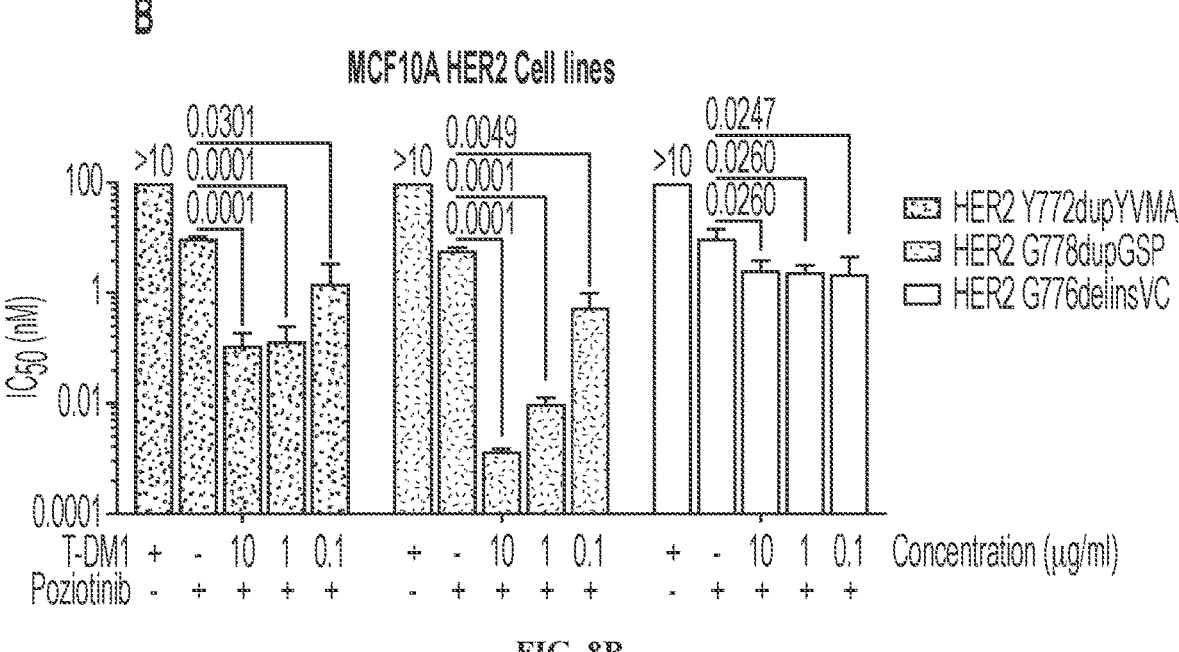
Figure 8C:
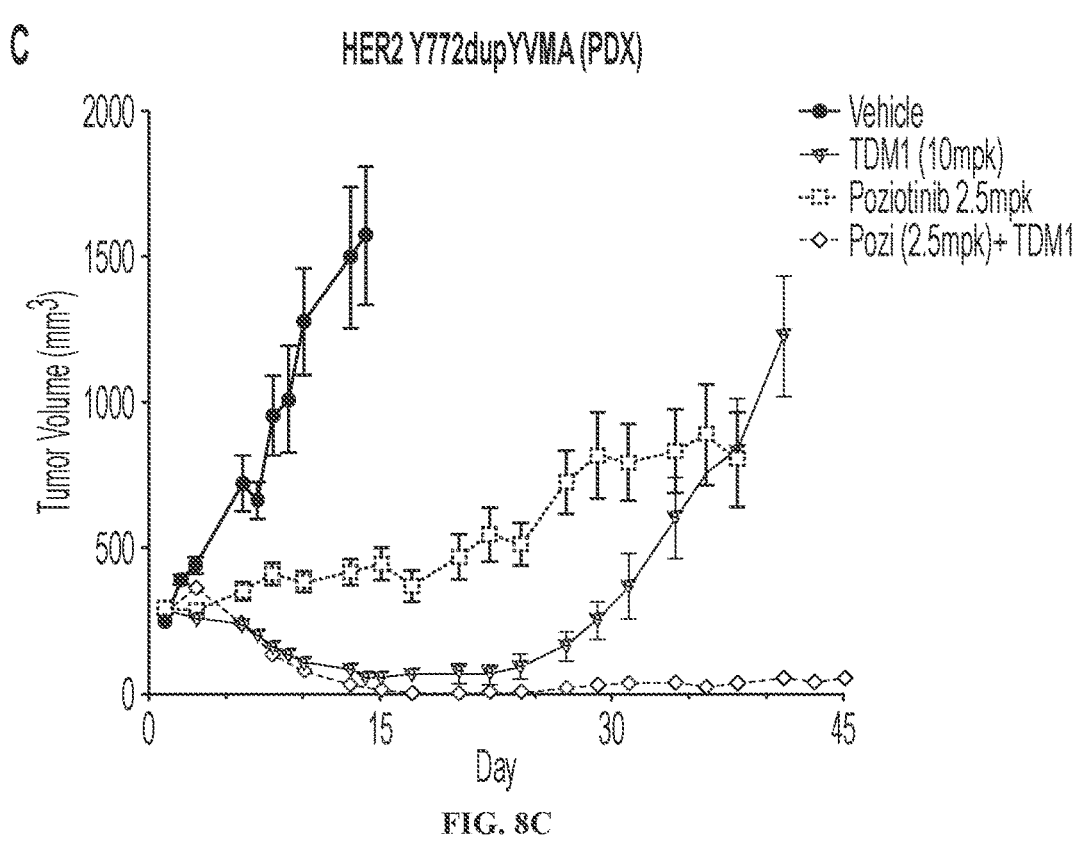
Figure 8D:
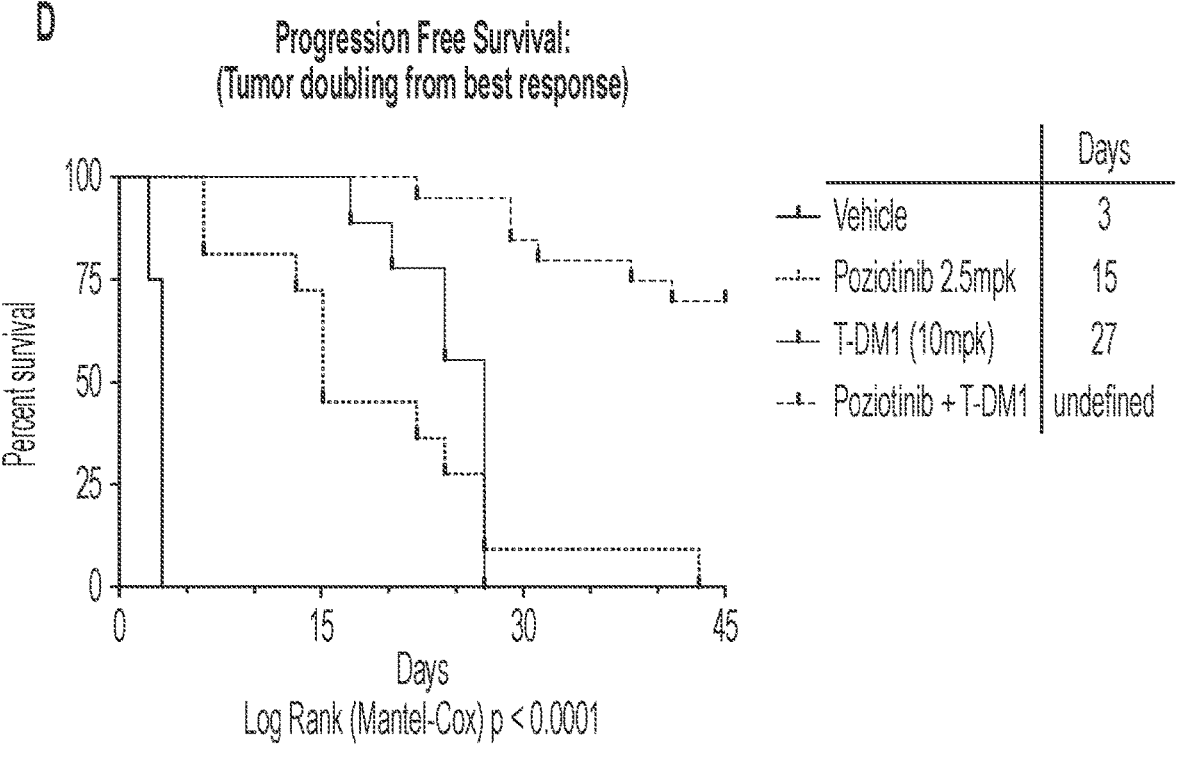
Figures 8E, 8F:
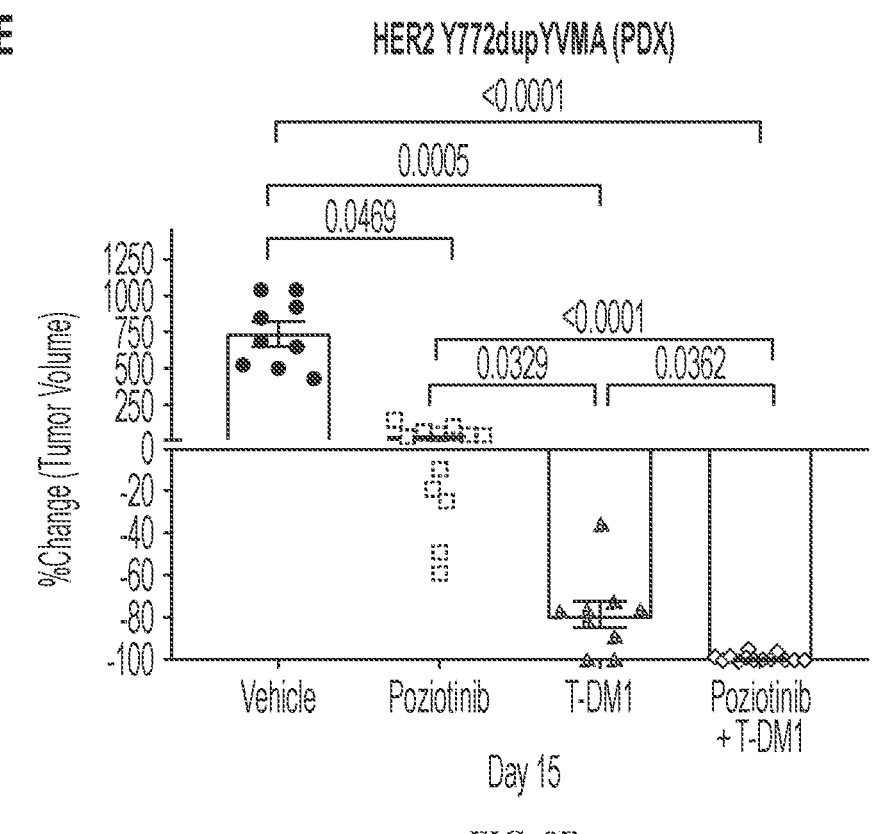
Figure 8G:
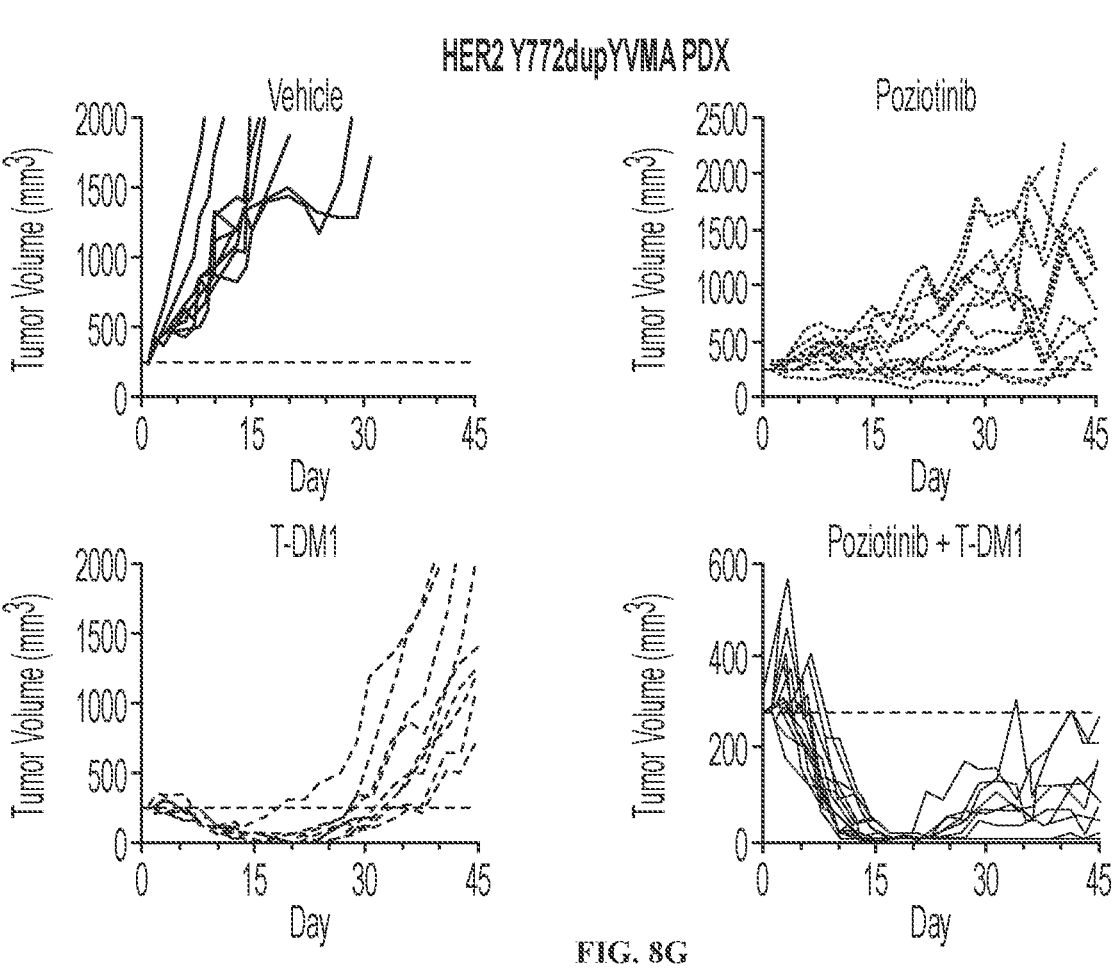

Combination of poziotinib and T-DM1 treatment potentiates anti-tumor activity: Previous studies of HER2 TKI lapatinib in HER2-positive breast cancer models and EGFR inhibitors in EGFR mutant NSCLC models have shown that TKI treatment results in an increase of receptor accumulation on the cell surface, and that increased cell surface HER2/EGFR increases sensitivity to antibody-dependent cellular cytotoxicity (ADCC). To determine if poziotinib treatment increases total HER2 receptor expression on the cell surface cell surface HER2 expression was analyzed by FACS after 24 hours of low dose poziotinib treatment. It was found that, on average, poziotinib treatment increased cell surface HER2 expression 2-fold (FIG. 8A, p<0.0001). Next, it was tested whether the combination of poziotinib and T-DM1 would decrease cell viability in vitro, and it was found that while T-DM1 alone did not inhibit cell viability of MCF10A HER2 mutant cell lines, combination of T-DM1 with poziotinib resulted in significantly lower $IC_{50}$ values than either agent alone in a dose-dependent manner (FIG. 8B). To validate these findings in vivo, the combination of low dose poziotinib with a single dose of T-DM1 was tested in a HER2 mutant NSCLC PDX model, HER2 Y772dupYVMA (FIG. 8C). To asses response to treatment, progression free survival (PFS) was determined, defined as time to tumor doubling from best response. Mice receiving vehicle control had a median PFS (mPFS) of 3 days, whereas mice receiving low dose poziotinib or T-DM1 had an mPFS of 15 days and 27 days, respectively. However, (14/20) mice receiving a single dose of T-DM1 in combination with low dose poziotinib remained tumor free at 45 days (FIG. 8D). Furthermore, at the time of best response, day 15, the combination of low dose poziotinib (2.5 mg/kg) and a single dose of T-DM1 (10 mg/kg) resulted in complete tumor regression in 20/20 mice (100%), compared to 2/9 mice receiving T-DM1 alone or 0/12 mice receiving low dose poziotinib (FIGS. 8C-F). By day 30, tumor growth resumed in all mice receiving T-DM1 alone; however, in 14/20 mice receiving combination treatment there was no evidence of tumor reoccurrence (FIGS. 8F, G).

Here, it is reported that HER2 mutations occur in various tumor types although the specific mutational hotspots vary by malignancy. Moreover, sensitivity to HER2 TKIs is heterogeneous across mutation location, with HER2 exon 20 insertions and L755P mutations being resistant to the majority of HER2 TKIs, likely due to the reduced volume of the drug binding pocket. Furthermore, poziotinib was identified as a potent, pan-HER2 mutant-selective inhibitor with clinical efficacy in NSCLC patients bearing HER2 exon 20 insertions and L755P mutations. Lastly, it was established that poziotinib treatment induced accumulation of HER2 on the cell surface, and that combination of poziotinib and T-DM1 treatment enhanced anti-tumor activity in vitro and in vivo.

The pan-cancer analysis reveals that HER2 mutational hotspots vary by cancer type and have differential sensitivity to HER2 TKIs in vitro, which will likely affect clinical efficacy. In the SUMMIT trial, neratinib yielded the most efficacy in breast cancer patients, with the majority of responders being positive for L755S, V777L, or L869R mutations. In the in vitro Ba/F3 drug screening, these mutations correlated with low $IC_{50}$ values. In contrast, patients with colorectal cancer did not respond to neratinib. Consistent with this clinical observation, it was found that the V842I mutation is the most common HER2 mutation in colorectal cancer cases, and this specific mutation was not sensitive to neratinib in the drug screen assays. These data suggest that differential TKI sensitivities between malignancies may be, in part, explained by cancer-specific mutational hotspots, which directly impact drug sensitivity. However, key questions remain regarding why the distributions of HER2 mutations vary by tumor type and whether a given mutation yields a similar drug response in different tumor types. Data from the SUMMIT trial showed that while specific exon 20 insertions were associated with neratinib sensitivity in breast cancer patients, these identical mutations were associated with resistance in all other cancer types demonstrating that there may be potential mechanisms underlying these tumor-type specific differences in sensitivities that merit further investigation.

Exon 20 insertion mutations and the exon 19 L755P mutation are resistant to most HER2 TKIs. The in vitro drug screening revealed that exon 20 insertion mutations and the L755P mutation had the highest $IC_{50}$ values for each TKI tested. Molecular dynamic simulations revealed that these mutations induce conformational changes that affect the overall size and mobility of the drug binding pocket. Collectively, these in vitro and in silico findings are consistent with the clinical observations that patients with HER2 exon 20 insertion mutations historically have had poor responses to TKIs. In lung cancer, where exon 20 insertions frequently occur, patients harboring HER2 exon 20 insertion mutations had response rates of 0%, 11.5%, and 18.2%-18.8% to neratinib, dacomitinib, and afatinib, respectively. Moreover, while L755S mutations have been shown to respond to neratinib, L755P mutations are profoundly resistant to both TKIs, and antibody-drug conjugates.

Example 2—Materials and Methods

Analysis of HER2 mutation prevalence and variant frequency: To determine the frequencies of each HER2 mutation reported in databases from MD Anderson Cancer Center, cBioPortal, Foundation Medicine, or Guardant Health, each database was queried individually, then frequencies were weighted by the total number of patients in each database and are reported as weighted averages. To determine the frequency of HER2 mutations across cancer types in cBioPortal, all non-overlapping studies were selected and exported. For overlapping studies, only the largest dataset was used. To determine HER2 mutation frequencies at MD Anderson Cancer Center, the Institute for Personalized Cancer Therapy database was queried for all HER2 mutations independent of cancer type. To determine the frequency of HER2 exon 20 mutations from Foundation Medicine, de-identified data of the number of patients with HER2 deletions, frame shifts, insertions, and point mutation were tabulated, and cancer types with less than 5 mutations were excluded. Lastly, to determine the frequency of HER2 exon 20 mutations at Guardant Health, the Guardant360 clinical database was queried for samples tested between October 2015 and May 2018 (70 and 73 gene panels) with an ERBB2 exon 20 mutation. Guardant360® is a CLIA—certified, CAP/NYSDOH accredited comprehensive cfDNA NGS test that reports out SNVs, indels, fusions, and SNVs in up to 73 genes. Frequencies reported from Guardant Health were then normalized to correct for clinical sensitivity as reported in Odegaard et al 2018. Specifically, frequencies were divided by the percent clinical sensitivity, 85.9%.

Ba/F3 Cell line generation and IL-3 deprivation: Ba/F3 cell lines were established as previously described (Robichaux et al., 2018). Briefly, stable Ba/F3 cell lines were generated by retroviral transduction of Ba/F3 cell line for 12 hours. Retroviruses were generated by transfecting pBabe-Puro based vectors summarized in Table 1 (Addgene and Bioinnovatise) into Phoenix 293T-ampho cells (Orbigen) using Lipofectamine 2000 (Invitrogen). Three days after transduction, 2 μg/ml puromycin (Invitrogen) was added to the RPMI media. After 5 days of selection, cells were stained with FITC-HER2 (Biolegend) sorted by FACS. Cell lines were then grown in the absence of IL-3 for two weeks and cell viability was assessed every three days using the Cell Titer Glo assay (Progema). Resulting stable cell lines were maintained in RPMI-1640 media containing 10% FBS without IL-3.

Cell Viability Assay and $IC_{50}$ Estimation: Cell viability was determined using the Cell Titer Glo assay (Promega) as previously described (Robichaux et al., 2018). Briefly, 2000-3000 cells per well were plated in 384-well plates (Greiner Bio-One) in technical triplicate. Cells were treated with seven different concentrations of tyrosine kinase inhibitors or vehicle alone at a final volume of 40 μL per well. After 3 days, 11μL of Cell Titer Glo was added to each well. Plates were shaken for 15 minutes, and bioluminescence was determined using a FLUOstar OPTIMA multi-mode microplate reader (BMG LABTECH). Bioluminescence values were normalized to DMSO treated cells, and normalized values were plotted in GraphPad Prism using non-linear regression fit to normalized data with a variable slope. $IC_{50}$ values were calculated by GraphPad Prism at 50% inhibition.

ELISA for phospho- and total-HER2 and Correlation with IC50 Values: Protein was harvested from the parental Ba/F3 cell line and each of the Ba/F3 cell lines expressing HER2 mutations as described above. 5 μg/ml of protein was added to each ELISA plate and ELISA was performed as described by the manufacture instructions for phosphorylated HER2 Cell signaling, (#7968) and total HER2 (Cell Signaling, #7310). Relative p-HER2 expression was determined by taking the ratio of p-HER2 over total HER2 as determined by ELISA. The relative p-HER2 ratio was plotted against poziotoinib IC50 values calculated as described above. Pearson correlations and p-values were determined by GraphPad Prism.

Tyrosine Kinase Inhibitors and T-DM1: All inhibitors were purchased from Selleck Chemical with the exception of EGF816 and pyrotinib which were purchased from MedChem Express. All inhibitors were dissolved in DMSO at a concentration of 10 mM and stored at −80° C. Inhibitors were limited to two freeze thaw/cycle before being discarded. T-DM1 was purchased reconstituted from the M.D. Anderson Cancer Center institutional pharmacy.

Molecular Dynamics Simulations: Protein structural models of the HER2 mutants were constructed using the MOE computer program (Chemical Computing Group) by introducing in silico mutations to the PDB 3PP0 X-ray structure. Classical and accelerated molecular dynamics simulations were performed using the NAMD simulation package. Additional detail is provided in the Supplemental Information section.

Human Cell lines: MCF10A cells were purchased from ATCC and were cultured in DMEM/F12 media supplemented with 1% penicillin/streptomycin, 5% horse serum (sigma), 20 ng/ml EGF, 0.5 mg/ml hydrocortisone, and 10 μg/ml insulin. Stable cell lines were created by retroviral transduction, and retroviruses were generated by transfecting pBabe-Puro based vectors summarized in Table 1 (Addgene and Bioinnovatise) into Phoenix 293T-ampho cells (Orbigen) using Lipofectamine 2000 (Invitrogen). Two days after transduction, 0.5 μg/ml puromycin (Invitrogen) was added to the RPMI media. After 14 days of selection, cells were tested in cell viability assays as described above. CW-2 cells were provided by the Riken cell line database under MTA, and were maintained in RPMI containing 10% FBS and 1% penicillin/streptomycin.

In vivo xenograft studies: CW-2 cell line xenografts were created by injecting $1 \times 10^6$ cells in 50% matrigel into 6 week old female nu/nu nude mice. When tumors reached 350 mm³ mice were randomized into 4 groups: 20 mg/kg afatinib, 5 mg/kg poziotinib, 30 mg/kg neratinib, or vehicle control (0.5% Methylcellulose, 2% Tween-80 in dH2O). Tumor volumes were measured three times per week. Mice received drug Monday-Friday (5 days per week), but began dosing on Wednesday allowing for a 2 day holiday after the first 3 days of dosing.

Y772dupYVMA PDX mice were purchased from Jax Labs (Model #TM01446). Fragments from tumors expressing HER2 Y772dupYVMA were inoculated into 5- to 6-week old female NSG mice (Jax Labs #005557). Mice were measured three times per week, and when tumors reached a volume of 200-300 mm³ mice were randomized into four treatment groups: vehicle control (0.5% Methylcellulose, 0.05% Tween-80 in dH2O), 2.5 mg/kg poziotinib, 10 mg/kg T-DM1, or combination of 2.5 mg/kg poziotinib and 10 mg/kg T-DM1. Tumor volumes and body weight were measured three times per week. Mice treated with 2.5 mg/kg poziotinib received drug orally Monday-Friday (5 days per week). Mice treated with 10 mg/kg T-DM1 received one intravenous (IV) dose of T-DM1 on the day of randomization. Mice treated with combination poziotinib and T-DM1 received one IV dose of T-DM1 and began 2.5 mg/kg poziotinib five days per week, 3 days after the dose of T-DM1. Mice received a holiday from dosing if the mouse dropped in body weight by greater than 10% or if body weight dropped below 20 grams. Progression free survival was defined as tumor doubling from best response for two consecutive measurements. Complete regression was defined as greater than 95% reduction in tumor burden, and for mice with complete regression, tumor doubling was defined greater than 75 mm³ for more than two consecutive measurements. Experiments were completed in agreement with Good Animal Practices and with approval from MD Anderson Cancer Center Institutional Animal Care and Use Committee (Houston, TX).

TABLE 1

| Vectors used to generate stable cell lines | | |
| --- | --- | --- |
| Name | Mutation | Vendor |
| HER2 L755S | c.2264T > C | Created by Bioinnovatise from pBabe-puro HER2 WT from Addgene (#40978) |
| HER2 D769H | c.2305G > A | Created by Bioinnovatise from pBabe-puro HER2 WT from Addgene (#40978) |
| HER2 D769N | c.2305G > C | Created by Bioinnovatise from pBabe-puro HER2 WT from Addgene (#40978) |
| HER2 D769Y | c.2305G > T | Created by Bioinnovatise from pBabe-puro HER2 WT from Addgene (#40978) |
| HER2 Y772dupYVMA | c.2323_2324insTATGTCATGGCT (SEQ ID NO: 1) | Purchased from Addgene (#40982) |

TABLE 1-continued

Vectors used to generate stable cell lines

| Name | Mutation | Vendor |
|---|---|---|
| HER2 G776del insVC | c.2326_2328insTCT | Created by Bioinnovatise from pBabe-puro HER2 WT from Addgene (#40978) |
| HER2 G776del insVV | c.2327delinsTTGT | Created by Bioinnovatise from pBabe-puro HER2 WT from Addgene (#40978) |
| HER2 G776del insLC | c.2326G > TTGT | Created by Bioinnovatise from pBabe-puro HER2 WT from Addgene (#40978) |
| HER2 V773M | c.2317G > A | Created by Bioinnovatise from pBabe-puro HER2 WT from Addgene (#40978) |
| HER2 V777L | c.2329G > T | Created by Bioinnovatise from pBabe-puro HER2 WT from Addgene (#40978) |
| HER2 G778insLPS | c.2332_2333insGGCTCCCCA | Created by Bioinnovatise from pBabe-puro HER2 WT from Addgene (#40978) |
| HER2 P780insGSP | c.2339_2340insTGGCTCCCC | Created by Bioinnovatise from pBabe-puro HER2 WT from Addgene (#40978) |
| HER2 L786V | c. 2356C > G | Created by Bioinnovatise from pBabe-puro HER2 WT from Addgene (#40978) |
| HER2 V842I | c.2524G > A | Created by Bioinnovatise from pBabe-puro HER2 WT from Addgene (#40978) |
| HER2 L869R | c.2606T > G | Created by Bioinnovatise from pBabe-puro HER2 WT from Addgene (#40978) |

TABLE 2

Total number of patients by cancer type across databases.

| Cancer Type | Total N | Weighted Average frequency of HER2 mutations (FIG. 1A) | Weighted Average frequency of HER2 Exon 20 Mutations (FIG. 1B) |
|---|---|---|---|
| Bile Duct | 829 | 5.307% | 0.724% |
| Bladder | 3146 | 8.295% | 0.858% |
| Brain | 10105 | 0.350% | 0.040% |
| Breast | 29609 | 3.115% | 0.882% |
| Cervix | 1301 | | 0.384% |
| Colorectal | 33302 | 2.185% | 0.287% |
| Early Gastric Cancer | 341 | 3.812% | 0.293% |
| Endometrial | 4962 | 2.156% | 0.181% |
| Esophageal | 4824 | 2.902% | 0.435% |
| Head and Neck | 3428 | 1.083% | 0.146% |
| Kidney | 3600 | 1.164% | 0.167% |
| Leukemia | 2451 | 0.122% | 0.082% |
| Non-small Cell Lung Cancer | 7859 | 2.150% | 1.525% |
| Melanoma | 7409 | 0.892% | 0.165% |
| Neuroendocrine | 60085 | 0.896% | 0.121% |
| Ovarian | 11762 | 2.380% | 0.188% |
| Pancreatic | 7988 | 0.964% | 0.100% |
| Peritoneal | 693 | 0.937% | 0.433% |
| Prostate | 5319 | 1.154% | 0.019% |
| salivary gland | 962 | 0.303% | 0.832% |
| Sarcoma | 3198 | 0.534% | 0.063% |
| Small Cell | 2380 | | 0.336% |
| Small Intestine | 1028 | 4.730% | 1.751% |
| Stomach | 2969 | 4.515% | 0.370% |
| Thyroid | 2175 | 0.181% | 0.046% |

TABLE 3

Patient Characteristics and number of prior lines of therapy.

| Age | Sex | # of prior lines | Mutation |
|---|---|---|---|
| 57 | F | 1 | Y772_A775dupYVMA |
| 64 | F | 6 | Y772_A775dupYVMA |
| 54 | F | 1 | A775_G776insYVMA |
| 59 | F | 0 | Y772_A775dupYVMA |

TABLE 3-continued

Patient Characteristics and number of prior lines of therapy.

| Age | Sex | # of prior lines | Mutation |
|---|---|---|---|
| 58 | F | 3 | Y772_A775dupYVMA |
| 60 | F | 1 | G778_P780dupGSP |
| 61 | F | 3 | G778_P780dupGSP |
| 62 | F | 0 | A775_G776insYVMA |
| 55 | F | 2 | G778_P780dupGSP |
| 61 | M | 4 | Y772_A775dupYVMA |
| 63 | M | 1 | Y772_A775dupYVMA |
| 60 | F | 3 | Y772_A775dupYVMA |

FACS: MCF10A cells overexpressing HER2 mutations were plated overnight in a 6-well plate, then treated with 10 nM poziotinib. After 24 hours, cells were washed twice with PBS, and trypsinized. Cells were then resuspended in 0.5% FBS in PBS, and stained with anti-HER2-FITC antibody from Biolegend (#324404) for 45 minutes on ice. Cells were washed with 0.5% FBS in PBS twice, and analyzed by flow cytometry. IgG and unstained controls were used for gating.

Western Blotting: For Western blotting, cells were washed in PBS and lysed in RIPPA lysis buffer (ThermoFisher) and protease inhibitor cocktail tablets (Roche). Protein (30-40 µg) was loaded into gels purchased from BioRad. BioRad semi-dry transfer was used and then probed with antibodies against, pHER2, HER2, pPI3K, PI3K, p-AKT, AKT, p-ERK1/2, and ERK1/2 (1:1000; Cell Signaling). Blots were probed with antibodies against vinculin or β-actin (Sigma-Aldrich) as a loading control, and exposed using ECL Western Blotting substrate (Promega).

HER2 expression level and correlation with Ba/F3 mutant IC50. Protein was harvested from Ba/F cell lines, and ELISAs were performed as described by the manufacture instructions for total HER2 (Cell Signaling, #7310). Relative expression determined by ELISA was plotted against IC50 values calculated as described above. Pearson correlations and p-values were determined by GraphPad Prism.

Clinical Trial and CIND Identifiers: Patients provided written informed consent for treatment with poziotinib on either compassionate use protocol (MD Anderson Cancer Center CIND-18-0014) or clinical trial NCT03066206. The protocols are approved by both the MD Anderson Cancer Center institutional review board and the Food and Drug Administration.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Arcila et al., *Clin Cancer Res* 18:4910-8, 2012.
Arcila et al., *Mol Cancer Ther* 12(2):220-229, 2013.
Austin-Ward and Villaseca, *Revista Medica de Chile,* 126(7):838-845, 1998.
Ausubel et al., *Current Protocols in Molecular Biology,* John Wiley & Sons, New York, N.Y., 2003.
Bukowski et al., *Clinical Cancer Res.,* 4(10):2337-2347, 1998.
Camacho et al. *J Clin Oncology* 22(145): Abstract No. 2505 (antibody CP-675206), 2004.
Cha et al. *Int J Cancer* 130:2445-54, 2012.
Chee et al., *Science,* 274:610-614, 1996.
Cho et al., *Cancer Res* 73:6770-9, 2013.
Christodoulides et al., *Microbiology,* 144 (Pt 11):3027-3037, 1998.
Church and Gilbert, *Proc. Natl. Acad. Sci. USA* 81:1991-1995 (1988).
Cotton et al., *Proc. Natl. Acad. Sci. USA* 85:4397-4401 (1985).
Davidson et al., *J Immunother* 21(5):389-398, 1998.
Davies et al., *Plos One* 8, 2013.
Del Tito et al., *Clinical Chemistry* 44:731-739, 1998.
Drmanac et al., *Nat. Biotechnol.,* 16:54-58, 1998.
Drmanac et al., *Science,* 260:1649-1652, 1993.
Ettinger et al. *J Natl Compr Canc Netw* 16:807-21, 2018.
Flavell et al., *Cell* 15:25 (1978).
Fu et al., *Nat. Biotechnol.,* 16:381-384, 1998/Geever et al., *Proc. Natl. Acad. Sci. USA* 78:5081 (1981).
Hanibuchi et al., *Int. J. Cancer,* 78(4):480-485, 1998.
Hellstrand et al., *Acta Oncologica,* 37(4):347-353, 1998.
Hollander, *Front. Immun.,* 3:3, 2012.
Hong et al., *J Biol Chem* 282:19781-7, 2007.
Hui and Hashimoto, *Infection Immun.,* 66(11):5329-5336, 1998.
Hurwitz et al. *Proc Natl Acad Sci USA* 95(17): 10067-10071, 1998.
Hyman et al., *Nature* 554:189-94, 2018.
International Patent Publication No. WO 99/57318
International Patent Publication No. WO1995001994
International Patent Publication No. WO1998042752
International Patent Publication No. WO2000037504
International Patent Publication No. WO2001014424
International Patent Publication No. WO2009/101611
International Patent Publication No. WO2009/114335
International Patent Publication No. WO2010/027827
International Patent Publication No. WO2011/066342
International Patent Publication No. WO2015016718
International Patent Publication No. WO 00/37504

International Patent Publication No. WO01/14424
International Patent Publication No. WO98/42752
Kosaka et al., *Cancer Res* 2017.
Kris et al., *Ann Oncol* 26:1421-7, 2015.
Kris et al., *Ann Oncol* 26:1421-7, 2015.
Leal, M., *Ann N Y Acad Sci* 1321, 41-54, 2014.
Lynch et al., *N Engl J Med.* 350(21):2129-2139, 2004.
Ma et al., *J Clin Oncol* 33, 2015.
Maemondo et al., *N Engl J Med* 362:2380-8, 2010.
Meric-Bernstam et al., *Clin Cancer Res,* 2018.
Mitsudomi and Yatabe, *Cancer Sci.* 98(12):1817-1824, 2007.
Mokyr et al. *Cancer Res* 58:5301-5304, 1998.
Oxnard et al., *J Thorac Oncol.* 8(2):179-184, 2013.
Paez et al., *Science* 304(5676):1497-1500, 2004.
Pao et al., *Proc Natl Acad Sci USA* 101(36):13306-13311, 2004.
Pardoll, *Nat Rev Cancer,* 12(4): 252-64, 2012.
Perera et al., *Proc Natl Acad Sci USA* 106:474-9, 2009.
Qin et al., *Proc. Natl. Acad. Sci. USA,* 95(24):14411-14416, 1998.
Raca et al., *Genet Test* 8(4):387-94 (2004).
Robichaux et al., *Nat Med* 24:638-46, 2018.
Sanger et al., *Proc. Natl. Acad. Sci. USA* 74:5463-5467 (1977).
Sears et al., *Biotechniques,* 13:626-633, 1992.
Sheffield et al., *Proc. Natl. Acad. Sci. USA* 86:232-236 (1989).
Shen et al., *J Recept Signal Transduct Res* 36:89-97, 2016.
Thress et al., *Nat Med* 21:560-2, 2015.
U.S. Pat. No. 4,870,287
U.S. Pat. No. 5,288,644
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,869,245
U.S. Pat. No. 5,885,796
U.S. Pat. No. 6,207,156
U.S. Pat. No. 8,008,449
U.S. Pat. No. 8,017,114
U.S. Pat. No. 8,119,129
U.S. Pat. No. 8,188,102
U.S. Pat. No. 8,329,867
U.S. Pat. No. 8,354,509
U.S. Pat. No. 8,735,553
U.S. Patent Publication No. 2004/0014095
U.S. Patent Publication No. 2005/0260186
U.S. Patent Publication No. 2006/0104968
U.S. Patent Publication No. 20110008369
U.S. Patent Publication No. 20130071452
U.S. Patent Publication No. 2014022021
U.S. Patent Publication No. 20140294898
Underhill et al., *Genome Res.* 7:996-1005 (1997).
Vogel et al., *J Clin Oncol* 20:719-26, 2002.
Yang et al., *Int J Cancer* 2016.
Yasuda et al., *Sci Transl Med* 5(216):216ra177, 2013.
Zimmerman et al., *Methods Mol. Cell. Biol.,* 3:39-42, 1992.

What is claimed is:

1. A method of treating cancer in a subject comprising administering an effective amount of poziotinib to the subject, wherein the subject has been determined to have one or more HER2 exon 21 mutations at residues selected from the group consisting of V842 and L869.

2. The method of claim 1, wherein the poziotinib is further defined as poziotinib hydrochloride salt.

3. The method of claim 1, wherein the subject has been determined to have 2, 3, or 4 HER exon 21 mutations.

4. The method of claim 1, wherein the subject has been previously administered a tyrosine kinase inhibitor.

5. The method of claim 4, wherein the subject is resistant to the previously administered tyrosine kinase inhibitor.

6. The method of claim 1, wherein the one or more HER2 exon 21 mutations are at residue V842 .

7. The method of claim 1, wherein the subject has been determined to not have an EGFR mutation at residue C797.

8. The method of claim 1, wherein the one or more HER2 exon 21 mutations are V842I or L869R.

9. The method of claim 1, wherein the one or more HER2 exon 21 mutation is V842I.

10. The method of claim 1, wherein the poziotinib is administered at a dose of 8 mg, 12 mg, or 16 mg.

11. The method of claim 1, further comprising administering an additional anti-cancer therapy.

12. The method of claim 11, wherein the additional anti-cancer therapy is chemotherapy, radiotherapy, gene therapy, surgery, hormonal therapy, anti-angiogenic therapy or immunotherapy.

13. The method of claim 1, wherein the cancer is oral cancer, oropharyngeal cancer, nasopharyngeal cancer, respiratory cancer, urogenital cancer, gastrointestinal cancer, central nervous system tissue cancer, peripheral nervous system tissue cancer, an endocrine cancer, neuroendocrine cancer, hematopoietic cancer, sarcoma, lymphoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer.

14. The method of claim 1, wherein the cancer is non-small cell lung cancer.

* * * * *

SEQUENCE LISTING

<160> NUMBER OF SEQ ID NOS: 1

<210> SEQ ID NO 1
<211> LENGTH: 12
<212> TYPE: DNA
<213> ORGANISM: Artificial sequence
<220> FEATURE:
<223> OTHER INFORMATION: Synthetic oligo

<400> SEQUENCE: 1
tatgtcatgg ct                                                                              12